United States Patent [19]
Anthony et al.

[11] Patent Number: 6,093,737
[45] Date of Patent: Jul. 25, 2000

[54] INHIBITORS OF FARNESYL-PROTEIN TRANSFERASE

[75] Inventors: Neville J. Anthony, Hatfield; Robert P. Gomez, Perkasie; Lekhanh O. Tran, Norristown; Steven D. Young, Lansdale, all of Pa.

[73] Assignee: Merck & Co., Inc., Rahway, N.J.

[21] Appl. No.: 08/997,171

[22] Filed: Dec. 23, 1997

Related U.S. Application Data

[60] Provisional application No. 60/033,991, Dec. 30, 1996.

[51] Int. Cl.$^7$ .......................... C07D 401/06; A61K 31/44
[52] U.S. Cl. ................... 514/341; 546/272.7; 546/274.1; 546/274.4; 546/274.7; 546/275.1; 546/256; 544/333; 544/405; 514/333; 514/256; 514/255
[58] Field of Search ............................. 546/272.7, 274.1, 546/274.4, 274.7, 275.1; 514/341

[56] References Cited

U.S. PATENT DOCUMENTS

| | | | |
|---|---|---|---|
| 4,074,051 | 2/1978 | Stevens | 544/140 |
| 4,287,195 | 9/1981 | Heeres et al. | 544/366 |
| 4,329,470 | 5/1982 | Grisar et al. | 546/210 |
| 4,713,387 | 12/1987 | Watanabe et al. | 514/332 |
| 4,826,835 | 5/1989 | Kuhla et al. | 514/252 |
| 4,914,207 | 4/1990 | Nagel et al. | 546/167 |
| 5,428,164 | 6/1995 | Thurkauf et al. | 544/295 |
| 5,441,970 | 8/1995 | Reitz et al. | 514/340 |
| 5,478,934 | 12/1995 | Yuan et al. | 540/546 |
| 5,616,601 | 4/1997 | Khanna et al. | 514/399 |
| 5,646,280 | 7/1997 | Thurkauf et al. | 544/295 |
| 5,656,762 | 8/1997 | Thurkauf et al. | 544/370 |

FOREIGN PATENT DOCUMENTS

| | | |
|---|---|---|
| 0 393 607 A2 | 10/1990 | European Pat. Off. . |
| 0 508 393 A1 | 10/1992 | European Pat. Off. . |
| 0 612 731 A1 | 8/1994 | European Pat. Off. . |
| WO 94/08990 | 4/1994 | WIPO . |
| WO 96/32938 | 10/1996 | WIPO . |
| WO 96/34851 | 11/1996 | WIPO . |
| WO 97/36890 | 10/1997 | WIPO . |
| WO 97/36896 | 10/1997 | WIPO . |
| WO 97/36897 | 10/1997 | WIPO . |
| WO 97/36898 | 10/1997 | WIPO . |
| WO 97/36901 | 10/1997 | WIPO . |

OTHER PUBLICATIONS

Exp. Opin, Ther. Patents, vol. 6, No. 12, pp. 1295–1304 (1996), by S. Graham, et al.
Exp. Opin. Ther. Patents, vol. 5, No. 12, pp. 1269–1285 (1995), by S. L. Graham.
Cancer Research, vol. 55, pp. 5302–5309 (1995), by L. Sepp–Lorenzino et al.
Nature Medicine, vol. 1, No. 8, pp. 792–797 (1995), by N. Kohl, et al.
Proc. Natl. Acad. Sci. USA, vol. 91, pp. 9141–9145 (1994), by N. Kohl, et al.
J. of Biol. Chem., vol. 270, No. 11, pp. 6221–6226 (1995), by G. James, et al.
J. of Biol. Chem., vol. 269, No. 44, pp. 27705–27714 (1994), by G. James, et al.
J. of Biol. Chem., vol. 265, No. 11, pp. 7617–7620 (1993), by J. Gibbs, et al.
Science, vol. 260, pp. 1934–1937 (1993), by N. Kohl, et al.
Derwent Abstract 90–318321/42 (Takeda) abstract of JP 02229169 Sep. 1990, PCT Examiner's search result for JP 02229169.

*Primary Examiner*—Jane Fan
*Attorney, Agent, or Firm*—David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

20 Claims, No Drawings

INHIBITORS OF FARNESYL-PROTEIN TRANSFERASE

This application claims the benefit under 35 119e provisional application 60/033991 Dec. 30, 1996.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in four general classes (S. Graham, *Expert Opinion Ther. Patents*, (1995) 5:1269–1285). The first are analogs of farnesyl diphosphate (FPP), while a second class of inhibitors is related to the protein substrates (e.g., Ras) for the enzyme. Bisubstrate inhibitors and inhibitors of farnesyl-protein transferase that are non-competitive with the substrates have also been described. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

Recently, certain tricyclic compounds which optionally incorporate a piperidine moiety have been disclosed to be inhibitors of FPTase (WO 95/10514, WO 95/10515 and WO 95/10516). Imidazole-containing compounds which are claimed to be inhibitors of farnesyl protein transferase have also been disclosed (WO 95/09001 and EP 0 675 112 A1). WO 95/09001 discloses imidazolyl containing compounds that are inhibitors of farnesyl protein transferase.

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP H7-112930).

It is, therefore, an object of this invention to develop low molecular weight compounds that will inhibit farnesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention comprises bicyclic compounds which inhibit the farnesyl-protein transferase. Further contained in this invention are chemotherapeutic compositions containing these farnesyl transferase inhibitors and methods for their production.

The compounds of this invention are illustrated by the formula A:

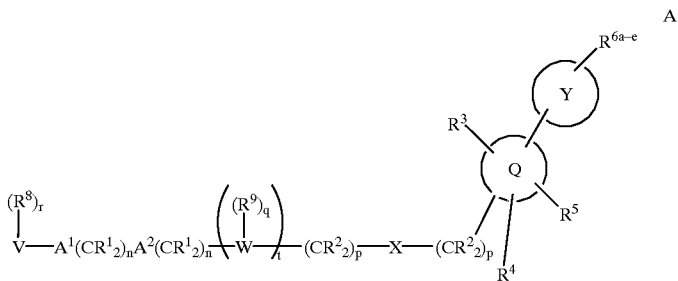

DETAILED DESCRIPTION OF THE INVENTION

The compounds of this invention are useful in the inhibition of farnesyl-protein transferase and the farnesylation of the oncogene protein Ras. In a first embodiment of this invention, the inhibitors of farnesyl-protein transferase are illustrated by the formula A:

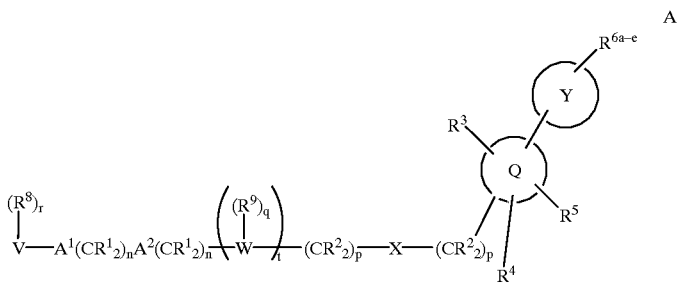

wherein:

Q is a 4, 5, 6 or 7 membered heterocyclic ring which comprises a nitrogen atom through which Q is attached to Y and 0–2 additional heteroatoms selected from N, S and O, and which also comprises a carbonyl, thiocarbonyl, —C(=NR$^{13}$)— or sulfonyl moiety adjacent to the nitrogen atom attached to Y, provided that Q is not

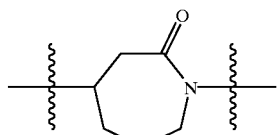

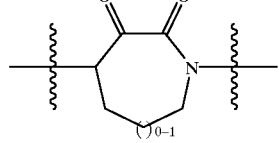

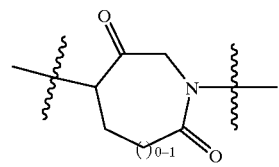

or

-continued

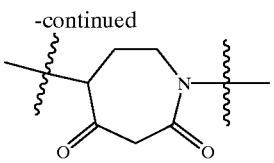

Y is a 5, 6 or 7 membered carbocyclic ring wherein from 0 to 3 carbon atoms are replaced by a heteroatom selected from N, S and O, and wherein Y is attached to Q through a carbon atom;

R$^1$ and R$^2$ are independently selected from:
a) hydrogen,
b) aryl, heterocycle, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, R$^{11}$C(O)O—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
c) unsubstituted or substituted C$_1$–C$_6$ alkyl wherein the substituent on the substituted C$_1$–C$_6$ alkyl is selected from unsubstituted or substituted aryl, heterocyclic, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, and R$^{11}$OC(O)-NR$^{10}$—;

R$^3$, R$^4$ and R$^5$ are independently selected from:
a) hydrogen,
b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, halogen, C$_1$–C$_6$ perfluoroalkyl, $R^{12}O-$, $R^{11}S(O)_m-$, $R^{10}C(O)NR^{10}-$, $(R^{10})_2NC(O)-$, $R^{11}C(O)O-$, $R^{10}{}_2N-C(NR^{10})-$, CN, NO$_2$, $R^{10}C(O)-$, N$_3$, $-N(R^{10})_2$, or $R^{11}OC(O)NR^{10}-$, c) unsubstituted $C_1-C_6$ alkyl, d) substituted $C_1-C_6$ alkyl wherein the substituent on the substituted $C_1-C_6$ alkyl is selected from unsubstituted or substituted aryl, unsubstituted or substituted heterocyclic, $C_3-C_{10}$ cycloalkyl, $C_2-C_6$ alkenyl, $C_2-C_6$ alkynyl, $R^{12}O-$, $R^{11}S(O)_m-$, $R^{10}C(O)NR^{10}-$, $(R^{10})_2NC(O)-$, $R^{10}{}_2N-C(NR^{10})-$, CN, $R^{10}C(O)-$, N$_3$, $-N(R^{10})_2$, and $R^{11}OC(O)-NR^{10}-$;

$R^{6a}$, $R^{6b}$, $R^{6c}$, $R^{6d}$ and $R^{6e}$ are independently selected from:

a) hydrogen, b) unsubstituted or substituted aryl, unsubstituted or substituted heterocycle, $C_3-C_{10}$ cycloalkyl, $C_2-C_6$ alkenyl, $C_2-C_6$ alkynyl, halogen, $C_1-C_6$ perfluoroalkyl, $R^{12}O-$, $R^{11}S(O)_m-$, $R^{10}C(O)NR^{10}-$, $(R^{10})_2NC(O)-$, $R^{11}C(O)O-$, $R^{10}{}_2N-C(NR^{10})-$, CN, NO$_2$, $R^{10}C(O)-$, $(R^{10})_2NS(O)_2-$, $R^{11}S(O)_mNR^{10}-$, N$_3$, $-N(R^{10})_2$, or $R^{11}OC(O)NR^{10}-$, c) unsubstituted $C_1-C_6$ alkyl, d) substituted $C_1-C_6$ alkyl wherein the substituent on the substituted $C_1-C_6$ alkyl is selected from unsubstituted or substituted aryl, unsubstituted or substituted heterocyclic, $C_3-C_{10}$ cycloalkyl, $C_2-C_6$ alkenyl, $C_2-C_6$ alkynyl, $R^{12}O-$, $R^{11}S(O)_m-$, $R^{10}C(O)NR^{10}-$, $(R^{10})_2NC(O)-$, $(R^{10})_2NS(O)_2-$, $R^{11}S(O)_mNR^{10}-$, $R^{10}{}_2N-C(NR^{10})-$, CN, $R^{10}C(O)-$, N$_3$, $-N(R^{10})_2$, and $R^{11}OC(O)-NR^{10}-$; or any two of $R^{6a}$, $R^{6b}$, $R^{6c}$, $R^{6d}$ and $R^{6e}$ on adjacent carbon atoms are combined to form a diradical selected from $-CH=CH-CH=CH-$, $-CH=CH-CH_2-$, $-(CH_2)_4-$ and $-(CH_2)_3-$;

$R^7$ is selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:

a) $C_{1-4}$ alkoxy, b) aryl or heterocycle, c)

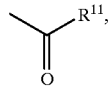

d) $-SO_2R^{11}$ e) $N(R^{10})_2$ or f) $C_{1-4}$ perfluoroalkyl;

$R^8$ is independently selected from:

a) hydrogen, b) aryl, substituted aryl, heterocycle, substituted heterocycle, $C_3-C_{10}$ cycloalkyl, $C_2-C_6$ alkenyl, $C_2-C_6$ alkynyl, perfluoroalkyl, F, Cl, Br, $R^{10}O-$, $R^{11}S(O)_m-$, $R^{10}C(O)NR^{10}-$, $(R^{10})_2NC(O)-$, $(R^{10})_2NS(O)_2-$, $R^{11}S(O)_mNR^{10}-$, $R^{10}{}_2N-C(NR^{10})-$, CN, NO$_2$, $R^{10}C(O)-$, N$_3$, $-N(R^{10})_2$, or $R^{11}OC(O)NR^{10}-$, and c) $C_1-C_6$ alkyl unsubstituted or substituted by aryl, cyanophenyl, heterocycle, $C_3-C_{10}$ cycloalkyl, $C_2-C_6$ alkenyl, $C_2-C_6$ alkynyl, perfluoroalkyl, F, Cl, Br, $R^{10}O-$, $R^{11}S(O)_m-$, $R^{10}C(O)NH-$, $(R^{10})_2NC(O)-$, $(R^{10})_2NS(O)_2-$, $R^{11}S(O)_mNR^{10}-$, $R^{10}{}_2N-C(NR^{10})-$, CN, $R^{10}C(O)-$, N$_3$, $-N(R^{10})_2$, or $R^{10}OC(O)NH-$;

$R^9$ is independently selected from:

a) hydrogen, b) alkenyl, alkynyl, perfluoroalkyl, F, Cl, Br, $R^{10}O-$, $R^{11}S(O)_m-$, $R^{10}C(O)NR^{10}-$, $(R^{10})_2NC(O)-$, $R^{10}{}_2N-C(NR^{10})-$, CN, NO$_2$, $R^{10}C(O)-$, N$_3$, $-N(R^{10})_2$, or $R^{11}OC(O)NR^{10}-$, and c) $C_1-C_6$ alkyl unsubstituted or substituted by perfluoroalkyl, F, Cl, Br, $R^{10}O-$, $R^{11}S(O)_m-$, $R^{10}C(O)NR^{10}-$, $(R^{10})_2NC(O)-$, $R^{10}{}_2N-C(NR^{10})-$, CN, $R^{10}C(O)-$, N$_3$, $-N(R^{10})_2$, or $R^{11}OC(O)NR^{10}-$;

$R^{10}$ is independently selected from hydrogen, $C_1-C_6$ alkyl, amino-$C_1-C_6$ alkyl, N-(unsubstituted or substituted benzolyl)-amino-$C_1-C_6$ alkyl, ($C_1-C_6$ alkyl)$_2$-amino-$C_1-C_6$ alkyl, acetylamino-$C_1-C_6$ alkyl, phenyl-$C_1-C_6$ alkyl, 2,2,2-trifluoroethyl, aryl and substituted aryl;

$R^{11}$ is independently selected from $C_1-C_6$ alkyl and aryl;

$R^{12}$ is independently selected from hydrogen, $C_1-C_6$ alkyl, $C_1-C_6$ aralkyl, $C_1-C_6$ substituted aralkyl, $C_1-C_6$ heteroaralkyl, $C_1-C_6$ substituted heteroaralkyl, aryl, substituted aryl, heteroaryl, substituted hetaryl, $C_1-C_6$ perfluoroalkyl, 2-aminoethyl and 2,2,2-trifluoroethyl;

$R^{13}$ is selected from hydrogen, $C_1-C_6$ alkyl, cyano, $C_1-C_6$ alkylsulfonyl and $C_1-C_6$ acyl;

$A^1$ and $A^2$ are independently selected from: a bond, $-CH=CH-$, $-C\equiv C-$, $-C(O)-$, $-C(O)NR^{10}-$, $-NR^{10}C(O)-$, O, $-N(R^{10})-$, $-S(O)_2N(R^{10})-$, $-N(R^{10})S(O)_2-$, or $S(O)_m$;

V is selected from:

a) hydrogen, b) heterocycle, c) aryl, d) $C_1-C_{20}$ alkyl wherein from 0 to 4 carbon atoms are replaced with a heteroatom selected from O, S, and N, and e) $C_2-C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

X is a bond, $-CH=CH-$, O, $-C(=O)-$, $-C(O)NR^7-$, $-NR^7C(O)-$, $-C(O)O-$, $-OC(O)-$, $-C(O)NR^7C(O)-$, $-NR^7-$, $-S(O)_2N(R^{10})-$, $-N(R^{10})S(O)_2-$ or $-S(=O)_m-$;

m is 0, 1 or 2;

n is independently 0, 1, 2, 3 or 4;

p is independently 0, 1, 2, 3 or 4;

q is 0, 1, 2 or 3;

r is 0 to 5, provided that r is 0 when V is hydrogen; and t is 0 or 1;

or a pharmaceutically acceptable salt thereof.

A preferred embodiment of the compounds of this invention is illustrated by the following formula A:

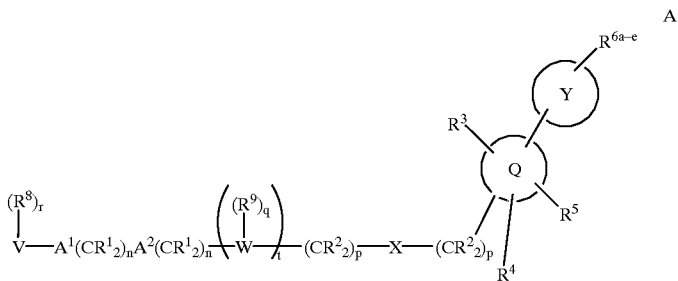

wherein:
Q is a 4, 5, 6 or 7 membered heterocyclic ring which comprises a nitrogen atom through which Q is attached to Y and 0–2 additional heteroatoms selected from N, S and O, and which also comprises a carbonyl, thiocarbonyl, —C(=NR$^{13}$)— or sulfonyl moiety adjacent to the nitrogen atom attached to Y, provided that Q is not

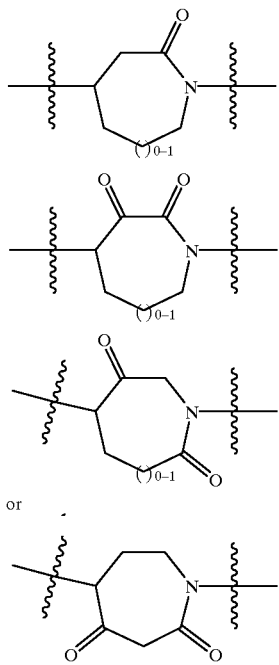

or

Y is selected from: phenyl, thienyl, pyridyl, pyrimidinyl, pyrazinyl, furyl, thiazolyl, isothiazolyl, tetrahydrofuryl, piperdinyl, thiazolidinyl, piperazinyl and tetrahydrothienyl;

$R^1$ is independently selected from: hydrogen, $C_3$–$C_{10}$ cycloalkyl, $R^{10}$O—, —N($R^{10}$)$_2$, F or $C_1$–$C_6$ alkyl;

$R^2$ is independently selected from:
  a) hydrogen,
  b) aryl, heterocycle, $C_3$–$C_{10}$ cycloalkyl, $R^{10}$O—, —N($R^{10}$)$_2$, F or $C_2$–$C_6$ alkenyl,
  c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^{10}$O— and —N($R^{10}$)$_2$;

$R^3$, $R^4$ and $R^5$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)NR$^{10}$—, ($R^{10}$)$_2$NC(O)—, $R^{10}{}_2$N—C(NR$^{10}$)—, CN, NO$_2$, $R^{10}$C(O)—, N$_3$, —N($R^{10}$)$_2$, or $R^{11}$OC(O)NR$^{10}$—,
  c) unsubstituted $C_1$–$C_6$ alkyl;
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)NR$^{10}$—, ($R^{10}$)$_2$NC(O)—, $R^{10}{}_2$N—C(NR$^{10}$)—, CN, $R^{10}$C(O)—, N$_3$, —N($R^{10}$)$_2$, and $R^{11}$OC(O)-NR$^{10}$—;

$R^{6a}$, $R^{6b}$, $R^{6c}$, $R^{6d}$ and $R^{6e}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)NR$^{10}$—, ($R^{10}$)$_2$NC(O)—, ($R^{10}$)$_2$NS(O)$_2$—, $R^{11}$S(O)$_m$NR$^{10}$—, $R^{10}{}_2$N—C(NR$^{10}$)—, CN, NO$_2$, $R^{10}$C(O)—, N$_3$, —N($R^{10}$)$_2$, or $R^{11}$OC(O)NR$^{10}$—,
  c) unsubstituted $C_1$–$C_6$ alkyl;
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)NR$^{10}$—, ($R^{10}$)$_2$NC(O)—, ($R^{10}$)$_2$NC(O)—, ($R^{10}$)$_2$NS(O)$_2$—, $R^{11}$S(O)$_m$NR$^{10}$—, $R^{10}{}_2$N—C(NR$^{10}$)—, CN, $R^{10}$C(O)—, N$_3$, —N($R^{10}$)$_2$, and $R^{11}$OC(O)—NR$^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

$R^7$ is selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
  a) $C_{1-4}$ alkoxy,
  b) aryl or heterocycle, c)

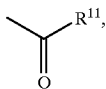

d) —SO$_2$R$^{11}$,
e) N(R$^{10}$)$_2$ or
f) C$_{1-4}$ perfluoroalkyl;

R$^8$ is independently selected from:
  a) hydrogen,
  b) aryl, substituted aryl, heterocycle, substituted heterocycle, C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, (R$^{10}$)$_2$NC(O)—, CN, NO$_2$, (R$^{10}$)$_2$N—C(NR$^{10}$)—, R$^{10}$C(O)—, (R$^{10}$)$_2$NS(O)$_2$—, R$^{11}$S(O)$_m$NR$^{10}$—, —N(R$^{10}$)$_2$, or R$^{11}$OC(O)NR$^{10}$—, and
  c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

R$^9$ is selected from:
  a) hydrogen,
  b) C$_2$–C$_6$ alkenyl, C$_2$–C$_6$ alkynyl, C$_1$–C$_6$ perfluoroalkyl, F, Cl, R$^{10}$O—, R$^{11}$S(O)$_m$—, R$^{10}$C(O)NR$^{10}$—, (R$^{10}$)$_2$NC(O)—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
  c) C$_1$–C$_6$ alkyl unsubstituted or substituted by C$_1$–C$_6$ perfluoroalkyl, F, Cl, R$^{10}$O—, R$^{11}$S(O)$_m$—, R$^{10}$C(O)NR$^{10}$—, (R$^{10}$)$_2$NC(O)—, CN, (R$^{10}$)$_2$N—C(NR$^{10}$)—, R$^{10}$C(O)—, —N(R$^{10}$)$_2$, or R$^{11}$OC(O)NR$^{10}$—;

R$^{10}$ is independently selected from hydrogen, C$_1$–C$_6$ alkyl, amino-C$_1$–C$_6$ alkyl, N-(unsubstituted or substituted benzoyl)-amino-C$_1$–C$_6$ alkyl, (C$_1$–C$_6$ alkyl)$_2$-amino-C$_1$–C$_6$ alkyl, acetylamino-C$_1$–C$_6$ alkyl, phenyl-C$_1$–C$_6$ alkyl, 2,2,2-trifluoroethyl, aryl and substituted aryl;

R$^{11}$ is independently selected from C$_1$–C$_6$ alkyl and aryl;

R$^{12}$ is independently selected from hydrogen, C$_1$–C$_6$ alkyl, C$_1$–C$_6$ aralkyl, C$_1$–C$_6$ substituted aralkyl, C$_1$–C$_6$ heteroaralkyl, C$_1$–C$_6$ substituted heteroaralkyl, aryl, substituted aryl, heteroaryl, substituted heteraryl, C$_1$–C$_6$ perfluoroalkyl, 2-aminoethyl and 2,2,2-trifluoroethyl;

A$^1$ and A$^2$ are independently selected from: a bond, —CH═CH—, —C≡C—, —C(O)—, —C(O)NR$^{10}$—, O, —N(R$^{10}$)—, or S(O)$_m$;

V is selected from:
  a) hydrogen,
  b) heterocycle selected from pyrrolidinyl, imidazolyl, imidazolinyl, pyridinyl, thiazolyl, pyridonyl, 2-oxopiperidinyl, oxazolyl, indolyl, quinolinyl, isoquinolinyl, triazolyl and thienyl,
  c) aryl,
  d) C$_1$–C$_{20}$ alkyl wherein from 0 to 4 carbon atoms are replaced with a heteroatom selected from O, S, and N, and
  e) C$_2$–C$_{20}$ alkenyl, and
provided that V is not hydrogen if A$^1$ is S(O)$_m$ and V is not hydrogen if A$^1$ is a bond, n is 0 and A$^2$ is S(O)$_m$;

W is a heterocycle selected from pyrrolidinyl, imidazolyl, imidazolinyl, pyridinyl, thiazolyl, pyridonyl, 2-oxopiperidinyl, oxazolyl, indolyl, quinolinyl, triazolyl or isoquinolinyl;

X is a bond, O, —C(═O)—, —CH═CH—, —C(O)NR$^7$—, —NR$^7$C(O)—, —NR$^7$—, —S(O)$_2$N(R$^{10}$)—, —N(R$^{10}$)S(O)$_2$— or —S(═O)$_m$—;

m is 0, 1 or 2;
n is independently 0, 1, 2, 3 or 4;
p is independently 0, 1, 2, 3 or 4;
q is 0, 1, 2 or 3;
r is 0 to 5, provided that r is 0 when V is hydrogen; and
t is 0 or 1;
or a pharmaceutically acceptable salt thereof.

A preferred embodiment of the compounds of this invention are illustrated by the formula B:

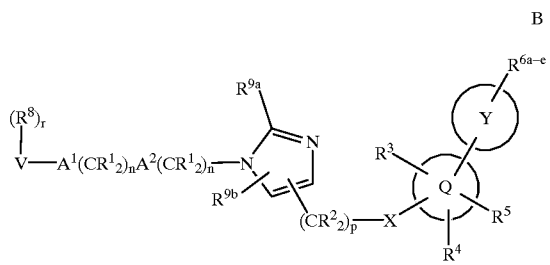

wherein:

Q is a 5 or 6 membered heterocyclic ring which comprises a nitrogen atom through which Q is attached to Y and 0–2 additional heteroatoms selected from N, S and O, and which also comprises a carbonyl or sulfonyl moiety adjacent to the nitrogen atom attached to Y, provided that Q is not

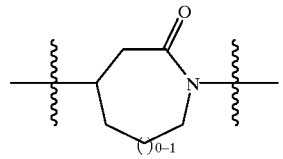

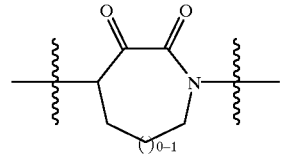

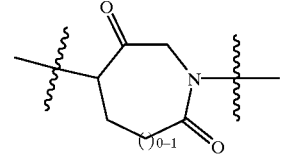

or

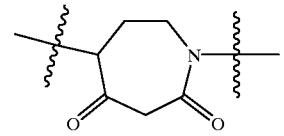

Y is selected from: phenyl, thiophenyl, pyridyl, pyrimidinyl, pyrazinyl, furyl, thiazolyl, isothiazolyl, tetrahydrofuryl, piperdinyl, thiazolidinyl, piperazinyl and tetrahydrothiophenyl;

R$^1$ is selected from: hydrogen, C$_3$–C$_{10}$ cycloalkyl, R$^{10}$O—, —N(R$^{10}$)$_2$, F or C$_1$–C$_6$ alkyl;

R$^2$ is independently selected from:

a) hydrogen,
b) aryl, heterocycle, $C_3$–$C_{10}$ cycloalkyl, $R^{10}O$—, —$N(R^{10})_2$, F or $C_2$–$C_6$ alkenyl,
c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^{10}O$— and —$N(R^{10})_2$;

$R^3$ and $R^4$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $(R^{10})_2NS(O)_2$—, $R^{11}S(O)_m NR^{10}$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $(R^{10})_2NS(O)_2$—, $R^{11}S(O)_m NR^{10}$—, $R^{10}{}_2N$—$C(NR^{10})$—, CN, $R^{10}C(O)$—, $N_3$, —$N(R^{10})_2$, and $R^{11}OC(O)$—$NR^{10}$—; or
any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—$CH_2$—, —$(CH_2)_4$— and —$(CH_2)_3$—;

$R^8$ is independently selected from:
a) hydrogen,
b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, $(R^{10})_2NC(O)$—, $(R^{10})_2NS(O)_2$—, $R^{11}S(O)_m NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $(R^{10})_2NS(O)_2$—, $R^{11}S(O)_m NR^{10}$—, $R^{10}C(O)$—, —$N(R^{10})_2$, or $R^{11}OC(O)NR^{10}$—;

$R^{9a}$ and $R^{9b}$ are independently hydrogen, $C_1$–$C_6$ alkyl, trifluoromethyl and halogen;

$R^{10}$ is independently selected from hydrogen, $C_1$–$C_6$ alkyl, amino-$C_1$–$C_6$ alkyl, N-(unsubstituted or substituted benzolyl)-amino-$C_1$–$C_6$ alkyl, ($C_1$–$C_6$ alkyl)$_2$-amino-$C_1$–$C_6$ alkyl, acetylamino-$C_1$–$C_6$ alkyl, phenyl-$C_1$–$C_6$ alkyl, 2,2,2-trifluoroethyl, aryl and substituted aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted hetaryl, $C_1$–$C_6$ perfluoroalkyl, 2-aminoethyl and 2,2,2-trifluoroethyl;

$A^1$ and $A^2$ are independently selected from: a bond, —CH=CH—, —C≡C—, —C(O)—, —C(O)NR$^{10}$—, O, —$N(R^{10})$—, or $S(O)_m$;

V is selected from:
a) hydrogen,
b) heterocycle selected from pyrrolidinyl, imidazolyl, imidazolinyl, pyridinyl, thiazolyl, pyridonyl, 2-oxopiperidinyl, oxazolyl, indolyl, quinolinyl, isoquinolinyl, triazolyl and thienyl,
c) aryl,
d) $C_1$–$C_{20}$ alkyl wherein from 0 to 4 carbon atoms are replaced with a heteroatom selected from O, S, and N, and
e) $C_2$–$C_{20}$ alkenyl, and
provided that V is not hydrogen if $A^1$ is $S(O)_m$ and V is not hydrogen if $A^1$ is a bond, n is 0 and $A^2$ is $S(O)_m$;

X is a bond, —CH=CH—, —C(O)NR$^{10}$—, —NR$^{10}$—C(O)—, —NR$^{10}$—, O or —C(=O)—;

m is 0, 1 or 2;

n is independently 0, 1, 2, 3 or 4;

p is 0, 1, 2, 3 or 4; and r is 0 to 5, provided that r is 0 when V is hydrogen;
or a pharmaceutically acceptable salt thereof.

Another preferred embodiment of the compounds of this invention are illustrated by the formula C:

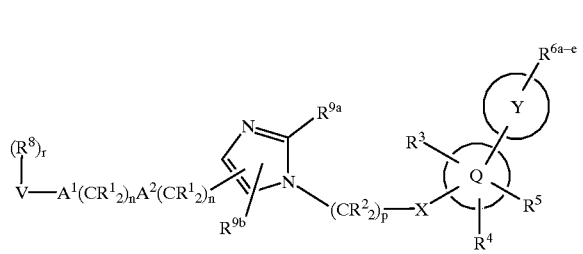

C wherein:
Q is a 5 or 6 membered heterocyclic ring which comprises a nitrogen atom through which Q is attached to Y and 0–2 additional heteroatoms selected from N, S and O, and which also comprises a carbonyl or sulfonyl moiety adjacent to the nitrogen atom attached to Y, provided that Q is not

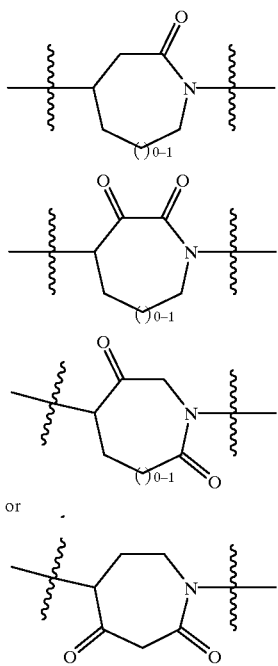

or

Y is selected from: phenyl, thiophenyl, pyridyl, pyrimidinyl, pyrazinyl, furyl, thiazolyl, isothiazolyl, tetrahydrofuryl, piperdinyl, thiazolidinyl, piperazinyl and tetrahydrothiophenyl;

$R^1$ is selected from: hydrogen, $C_3$–$C_{10}$ cycloalkyl, $R^{10}O$—, —$N(R^{10})_2$, F or $C_1$–$C_6$ alkyl;

$R^2$ is independently selected from:
  a) hydrogen,
  b) aryl, heterocycle, $C_3$–$C_{10}$ cycloalkyl, $R^{10}O$—, —$N(R^{10})_2$, F or $C_2$–$C_6$ alkenyl,
  c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^{10}O$— and —$N(R^{10})_2$;

$R^3$ and $R^4$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $CN(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)$—$NR^{10}$—;

$R^{6a}$, $R^{6b}$, $R^{6c}$, $R^{6d}$ and $R^{6e}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{11}S(O)_2NR^{10}$—, $(R^{10})_2NS(O)_2$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{11}S(O)_2NR^{10}$—, $(R^{10})_2NS(O)_2$—, $R^{10}_2N$—$C(NR^{10})$—, CN, $R^{10}C(O)$—, $N_3$, —$N(R^{10})_2$, and $R^{11}OC(O)$-$NR^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—$CH_2$—, —$(CH_2)_4$— and —$(CH_2)_3$—;

$R^8$ is independently selected from:
  a) hydrogen,
  b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, $(R^{10})_2NC(O)$—, $R^{11}S(O)_2NR^{10}$—, $(R^{10})_2NS(O)_2$—, CN, $NO_2$, $(R^{10})_2N$—$C(NR^{10})$—, $R^{10}C(O)$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2NC(O)$—, $R^{11}S(O)_2$ $NR^{10}$—, $(R^{10})_2NS(O)_2$—, $(R^{10})_2N$—$C(NR^{10})$—, $R^{10}C(O)$—, —$N(R^{10})_2$, or $R^{11}OC(O)NR^{10}$—;

$R^{9a}$ and $R^{9b}$ are independently hydrogen, $C_1$–$C_6$ alkyl, trifluoromethyl and halogen;

$R^{10}$ is independently selected from hydrogen, $C_1$–$C_6$ alkyl, amino-$C_1$–$C_6$ alkyl, N-(unsubstituted or substituted benzolyl)-amino-$C_1$–$C_6$ alkyl, ($C_1$–$C_6$ alkyl)$_2$-amino-$C_1$–$C_6$ alkyl, acetylamino-$C_1$–$C_6$ alkyl, phenyl-$C_1$–$C_6$ alkyl, 2,2,2-trifluoroethyl, aryl and substituted aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted hetaryl, $C_1$–$C_6$ perfluoroalkyl, 2-aminoethyl and 2,2,2-trifluoroethyl;

$A^1$ and $A^2$ are independently selected from: a bond, —CH=CH—, —C≡C—, —C(O)—, —C(O)$NR^{10}$—, O, —$N(R^{10})$—, or $S(O)_m$;

V is selected from:
  a) hydrogen,
  b) heterocycle selected from pyrrolidinyl, imidazolyl, imidazolinyl, pyridinyl, thiazolyl, pyridonyl, 2-oxopiperidinyl, oxazolyl, indolyl, quinolinyl, isoquinolinyl, triazolyl and thienyl,
  c) aryl,
  d) $C_1$–$C_{20}$ alkyl wherein from 0 to 4 carbon atoms are replaced with a heteroatom selected from O, S, and N, and
  e) $C_2$–$C_{20}$ alkenyl, and
provided that V is not hydrogen if $A^1$ is $S(O)_m$ and V is not hydrogen if $A^1$ is a bond, n is 0 and $A^2$ is $S(O)_m$;

X is a bond, —CH=CH—, —C(O)$NR^{10}$—, —$NR^{10}C(O)$—, —$NR^{10}$, O or —C(=O)—;

m is 0, 1 or 2;

n is independently 0, 1, 2, 3 or 4;

p is 0, 1, 2, 3 or 4, provided that p is not 0 if X is a bond or O;

and r is 0 to 5, provided that r is 0 when V is hydrogen;

or a pharmaceutically acceptable salt thereof.

In a more preferred embodiment of this invention, the inhibitors of farnesyl-protein transferase are illustrated by the formula D:

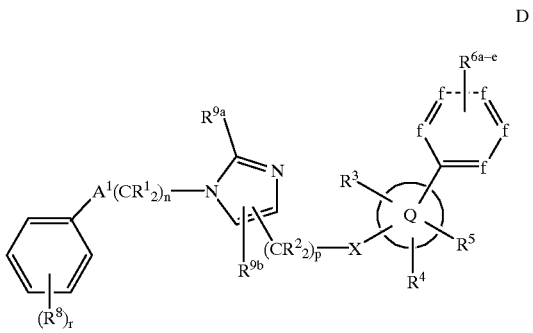

wherein:

Q is selected from

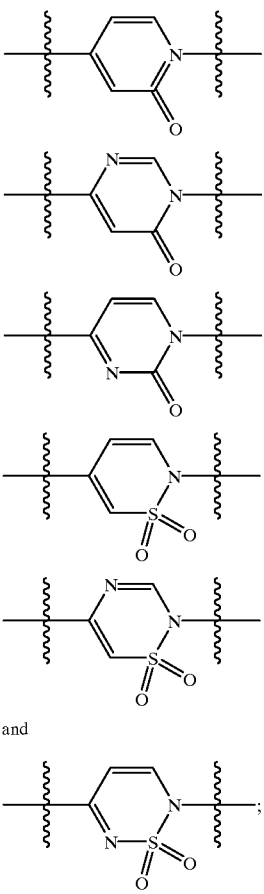

and

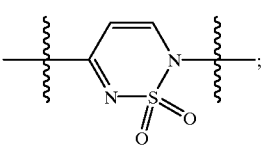

from 0–2 of f(s) are independently N, and the remaining f's are independently CH;

$R^1$ is selected from: hydrogen, $C_3$–$C_{10}$ cycloalkyl or $C_1$–$C_6$ alkyl;

$R^2$ is independently selected from:
a) hydrogen,
b) aryl, heterocycle, $C_3$–$C_{10}$ cycloalkyl, $R^{10}O$—, —$N(R^{10})_2$, F or $C_2$–$C_6$ alkenyl,
c) $C_1$–$C_6$ alkyl unsubstituted or substituted by aryl, heterocycle, $C_3$–$C_{10}$ cycloalkyl, $C_2$–$C_6$ alkenyl, $R^{10}O$—, or —$N(R^{10})_2$;

$R^3$ is selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2$ $NC(O)$—, $R^{10}_2N$—$C(NR^{10})$—, CN, $R^{10}C(O)$—, $N_3$, —$N(R^{10})_2$, and $R^{11}OC(O)$—$NR^{10}$—;

$R^4$ is selected from H, halogen, $C_1$–$C_6$ alkyl and $CF_3$;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)$—$NR^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—$CH_2$—, —$(CH_2)_4$— and —$(CH_2)_3$—;

$R^8$ is independently selected from:
a) hydrogen,
b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, $(R^{10})_2NC(O)$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2NC(O)$—, $(R^{10})_2N$—$C(NR^{10})$—, $R^{10}C(O)$—, —$N(R^{10})_2$, or $R^{11}OC(O)NR^{10}$—;

$R^{9a}$ and $R^{9b}$ are independently hydrogen, ethyl, cyclopropyl or methyl;

$R^{10}$ is independently selected from hydrogen, $C_1$–$C_6$ alkyl, amino-$C_1$–$C_6$ alkyl, N-(unsubstituted or substituted benzolyl)-amino-$C_1$–$C_6$ alkyl, $(C_1$–$C_6$ alkyl$)_2$-amino-$C_1$–$C_6$ alkyl, acetylamino-$C_1$–$C_6$ alkyl, phenyl-$C_1$–$C_6$ alkyl, 2,2,2-trifluoroethyl, aryl and substituted aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteraryl, $C_1$–$C_6$ perfluoroalkyl, 2-aminoethyl and 2,2,2-trifluoroethyl;

$A^1$ is selected from: a bond, —C(O)—, O, —N($R^{10}$)—, or S(O)$_m$;

X is a bond, —CH=CH—, —C(O)N$R^{10}$—, —N$R^{10}$C(O)—, —N$R^{10}$—, O or —C(=O)—, n is 0 or 1; provided that n is not 0 if $A^1$ is a bond, O, —N($R^{10}$)— or S(O)$_m$;

m is 0, 1 or 2;

p is 0, 1, 2, 3 or 4; and r is 0, 1 or 2;

or a pharmaceutically acceptable salt thereof.

In another more preferred embodiment of this invention, the inhibitors of farnesyl-protein transferase are illustrated by the formula E:

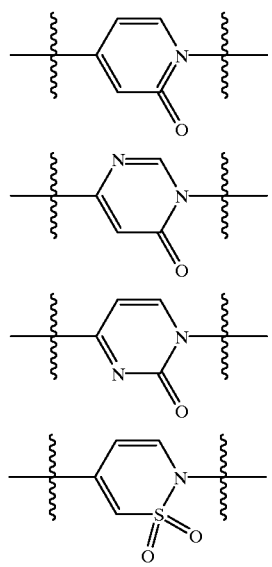

wherein:

Q is selected from

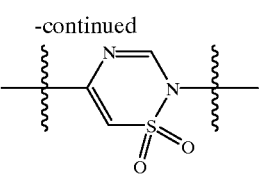

-continued

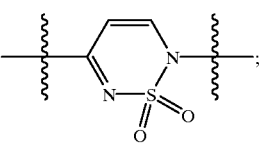

and

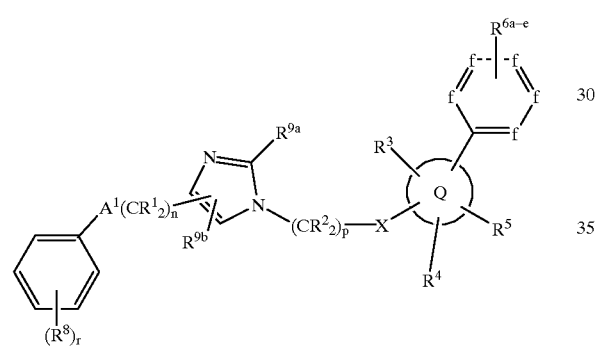

from 0–2 of f(s) are independently N, and the remaining f's are independently CH;

$R^1$ is selected from: hydrogen, $C_3$–$C_{10}$ cycloalkyl, $R^{10}$O—, —N($R^{10}$)$_2$, F or $C_1$–$C_6$ alkyl;

$R^2$ is independently selected from:
a) hydrogen,
b) aryl, heterocycle, $C_3$–$C_{10}$ cycloalkyl, $R^{10}$O—, —N($R^{10}$)$_2$, F or $C_2$–$C_6$ alkenyl,
c) $C_1$–$C_6$ alkyl unsubstituted or substituted by aryl, heterocycle, $C_3$–$C_{10}$ cycloalkyl, $C_2$–$C_6$ alkenyl, $R^{10}$O—, or —N($R^{10}$)$_2$;

$R^3$ is selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)N$R^{10}$—, ($R^{10}$)$_2$NC(O)—, $R^{10}{}_2$N—C(N$R^{10}$)—, CN, NO$_2$, $R^{10}$C(O)—, N$_3$, —N($R^{10}$)$_2$, or $R^{11}$OC(O)N$R^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)N$R^{10}$—, ($R^{10}$)$_2$NC(O)—, $R^{10}{}_2$N—C(N$R^{10}$)—, CN, $R^{10}$C(O)—, N$_3$, —N($R^{10}$)$_2$, and $R^{11}$OC(O)—N$R^{10}$—;

$R^4$ is selected from H, halogen, $C_1$–$C_6$ alkyl and CF$_3$;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)N$R^{10}$—, ($R^{10}$)$_2$NC(O)—, $R^{10}{}_2$N—C(N$R^{10}$)—, CN, NO$_2$, $R^{10}$C(O)—, N$_3$, —N($R^{10}$)$_2$, or $R^{11}$OC(O)N$R^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)(O)N$R^{10}$—, ($R^{10}$)$_2$NC(O)—, $R^{10}{}_2$N—C(N$R^{10}$)—, CN, $R^{10}$C(O)—, N$_3$, —N($R^{10}$)$_2$, and $R^{11}$OC(O)—N$R^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

R$^8$ is independently selected from:
a) hydrogen,
b) aryl, substituted aryl, heterocycle, substituted heterocycle, C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, (R$^{10}$)$_2$NC(O)—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
c) C$_1$–C$_6$ alkyl substituted by C$_1$–C$_6$ perfluoroalkyl, R$^{10}$O—, R$^{10}$C(O)NR$^{10}$—, (R$^{10}$)$_2$NC(O)—, (R$^{10}$)$_2$N—C(NR$^{10}$)—, R$^{10}$C(O)—, —N(R$^{10}$)$_2$, or R$^{11}$OC(O)NR$^{10}$—;

R$^{9a}$ and R$^{9b}$ are independently hydrogen, ethyl, cyclopropyl or methyl;

R$^{10}$ is independently selected from hydrogen, C$_1$–C$_6$ alkyl, amino-C$_1$–C$_6$ alkyl, N-(unsubstituted or substituted benzolyl)-amino-C$_1$–C$_6$ alkyl, (C$_1$–C$_6$ alkyl)$_2$-amino-C$_1$–C$_6$ alkyl, acetylamino-C$_1$–C$_6$ alkyl, phenyl-C$_1$–C$_6$ alkyl, 2,2,2-trifluoroethyl, aryl and substituted aryl;

R$^{11}$ is independently selected from C$_1$–C$_6$ alkyl and aryl;

R$^{12}$ is independently selected from hydrogen, C$_1$–C$_6$ alkyl, C$_1$–C$_6$ aralkyl, C$_1$–C$_6$ substituted aralkyl, C$_1$–C$_6$ heteroaralkyl, C$_1$–C$_6$ substituted heteroaralkyl, aryl, substituted aryl, heteroaryl, substituted heteraryl, C$_1$–C$_6$ perfluoroalkyl, 2-aminoethyl and 2,2,2-trifluoroethyl;

X is a bond, —CH=CH—, —C(O)NR$^{10}$—, —NR$^{10}$C(O)—, —NR$^{10}$—, O or —C(=O)—;

n is 0 or 1;

m is 0, 1 or 2;

p is 0, 1, 2, 3 or 4, provided that p is not 0 if X is a bond or O;

and r is 0, 1 or 2;

or a pharmaceutically acceptable salt thereof.

In a further embodiment of this invention, the inhibitors of farnesyl-protein transferase are illustrated by the formula F:

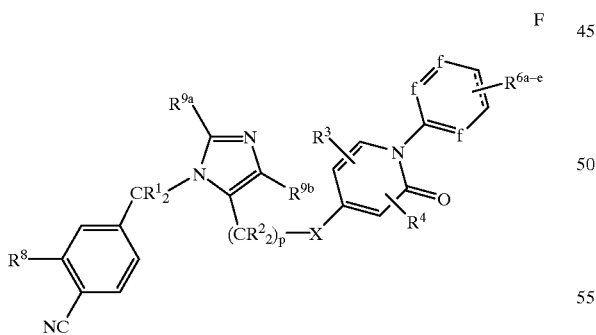

F wherein:
from 0–2 of f(s) are independently N, and the remaining f's are independently CH;

R$^1$ is selected from: hydrogen, C$_3$–C$_{10}$ cycloalkyl or C$_1$–C$_6$ alkyl;

R$^2$ is independently selected from:
a) hydrogen,
b) aryl, heterocycle, C$_3$–C$_{10}$ cycloalkyl, R$^{10}$O—, —N(R$^{10}$)$_2$ or F,
c) C$_1$–C$_6$ alkyl unsubstituted or substituted by aryl, heterocycle, C$_3$–C$_{10}$ cycloalkyl, R$^{10}$O—, or —N(R$^{10}$)$_2$;

R$^3$ is selected from:
a) hydrogen,
b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
c) unsubstituted C$_1$–C$_6$ alkyl,
d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, and R$^{11}$OC(O)NR$^{10}$—;

R$^4$ is selected from H, halogen, CH$_3$ and CF$_3$;

R$^{6a}$, R$^{6b}$, R$^{6c}$, R$^{6d}$ and R$^{6e}$ are independently selected from:
a) hydrogen,
b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
c) unsubstituted C$_1$–C$_6$ alkyl,
d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, and R$^{11}$OC(O)NR$^{10}$—; or any two of R$^{6a}$, R$^{6b}$, R$^{6c}$, R$^{6d}$ and R$^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

R$^8$ is independently selected from:
a) hydrogen,
b) aryl, substituted aryl, heterocycle, substituted heterocycle, C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, (R$^{10}$)$_2$NC(O)—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
c) C$_1$–C$_6$ alkyl substituted by C$_1$–C$_6$ perfluoroalkyl, R$^{10}$O—, R$^{10}$C(O)NR$^{10}$—, (R$^{10}$)$_2$NC(O)—, (R$^{10}$)$_2$N—C(NR$^{10}$)—, R$^{10}$C(O)—, —N(R$^{10}$)$_2$, or R$^{11}$OC(O)NR$^{10}$—;

R$^{9a}$ and R$^{9b}$ are independently hydrogen, ethyl, cyclopropyl or methyl;

R$^{10}$ is independently selected from hydrogen, C$_1$–C$_6$ alkyl, amino-C$_1$–C$_6$ alkyl, N-(unsubstituted or substituted benzolyl)-amino-C$_1$–C$_6$ alkyl, (C$_1$–C$_6$ alkyl)$_2$-amino-C$_1$–C$_6$ alkyl, acetylamino-C$_1$–C$_6$ alkyl, phenyl-C$_1$–C$_6$ alkyl, 2,2,2-trifluoroethyl, aryl and substituted aryl;

R$^{11}$ is independently selected from C$_1$–C$_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteraryl, $C_1$–$C_6$ perfluoroalkyl, 2-aminoethyl and 2,2,2-trifluoroethyl;

X is a bond, —CH=CH—, —C(O)NR$^{10}$—, —NR$^{10}$C(O)—, —NR$^{10}$—, O or —C(=O)—;

m is 0, 1 or 2; and p is 0, 1, 2, 3 or 4;

or a pharmaceutically acceptable salt thereof.

In a further embodiment of this invention, the inhibitors of farnesyl-protein transferase are illustrated by the formula G:

G wherein:

from 0–2 of f(s) are independently N, and the remaining f's are independently CH;

$R^1$ is selected from: hydrogen, $C_3$–$C_{10}$ cycloalkyl, $R^{10}$O—, —N(R$^{10}$)$_2$, F or $C_1$–$C_6$ alkyl;

$R^2$ is independently selected from:
  a) hydrogen,
  b) aryl, heterocycle or $C_3$–$C_{10}$ cycloalkyl,
  c) $C_1$–$C_6$ alkyl unsubstituted or substituted by aryl, heterocycle, $C_3$–$C_{10}$ cycloalkyl, $C_2$–$C_6$ alkenyl, $R^{10}$O—, or —N(R$^{10}$)$_2$;

$R^3$ is selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)NR$^{10}$—, (R$^{10}$)$_2$NC(O)—, $R^{10}{}_2$N—C(NR$^{10}$)—, CN, NO$_2$, $R^{10}$C(O)—, N$_3$, —N(R$^{10}$)$_2$, or $R^{11}$OC(O)NR$^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)NR$^{10}$—, (R$^{10}$)$_2$NC(O)—, $R^{10}{}_2$N—C(NR$^{10}$)—, CN, $R^{10}$C(O)—, N$_3$, —N(R$^{10}$)$_2$, and $R^{11}$OC(O)—NR$^{10}$—;

$R^4$ is selected from H, halogen, CH$_3$ and CF$_3$;

$R^{6a}$, $R^{6b}$, $R^{6c}$, $R^{6d}$ and $R^{6e}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)NR$^{10}$—, (R$^{10}$)$_2$NC(O)—, $R^{10}{}_2$N—C(NR$^{10}$)—, CN, NO$_2$, $R^{10}$C(O)—, N$_3$, —N(R$^{10}$)$_2$, or $R^{11}$OC(O)NR$^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)NR$^{10}$—, (R$^{10}$)$_2$NC(O)—, $R^{10}{}_2$N—C(NR$^{10}$)—, CN, $R^{10}$C(O)—, N$_3$, —N(R$^{10}$)$_2$, and $R^{11}$OC(O)—NR$^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

$R^8$ is independently selected from:
  a) hydrogen,
  b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}$O—, $R^{10}$C(O)NR$^{10}$—, (R$^{10}$)$_2$NC(O)—, CN, NO$_2$, (R$^{10}$)$_2$N—C(NR$^{10}$)—, $R^{10}$C(O)—, —N(R$^{10}$)$_2$, or $R^{11}$OC(O)NR$^{10}$—, and
  c) $C_1$–$C_6$ alkyl substituted by $C_1$–$C_6$ perfluoroalkyl, $R^{10}$O—, $R^{10}$C(O)NR$^{10}$—, (R$^{10}$)$_2$NC(O)—, (R$^{10}$)$_2$N—C(NR$^{10}$)—, $R^{10}$C(O)—, —N(R$^{10}$)$_2$, or $R^{11}$OC(O)NR$^{10}$—;

$R^{9a}$ and $R^{9b}$ are independently hydrogen, ethyl, cyclopropyl or methyl;

$R^{10}$ is independently selected from hydrogen, $C_1$–$C_6$ alkyl, amino-$C_1$–$C_6$ alkyl, N-(unsubstituted or substituted benzolyl)-amino-$C_1$–$C_6$ alkyl, ($C_1$–$C_6$ alkyl)$_2$-amino-$C_1$–$C_6$ alkyl, acetylamino-$C_1$–$C_6$ alkyl, phenyl-$C_1$–$C_6$ alkyl, 2,2,2-trifluoroethyl, aryl and substituted aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteraryl, $C_1$–$C_6$ perfluoroalkyl, 2-aminoethyl and 2,2,2-trifluoroethyl;

$A^1$ is selected from: a bond, —C(O)—, O, —N(R$^{10}$)—, or S(O)$_m$;

m is 0, 1 or 2; and n is 0 or 1;

or a pharmaceutically acceptable salt thereof.

The preferred compounds of the instant invention are selected from:

4-[3-(2-Oxo-1-phenyl-1,2-dihydropyridin-4-ylmethyl)-3H-imidazol-4-ylmethyl]benzonitrile 4-{3-[1-(3-Chloro-phenyl)-2-oxo-1,2-dihydropyridin-4-ylmethyl]-3H-imidazol-4-ylmethyl}benzonitrile 4-[3-(2-Oxo-2H-[1,2']bipyridinyl-4-ylmethyl)-3H-imidazol-4-ylmethyl]-benzonitrile 4-[3-(6'-Methyl-2-oxo-2H-[1,2']bipyridinyl-4-ylmethyl)-3H-imidazol-4-ylmethyl]-benzonitrile 4-{3-[1-(3-Chloro-phenyl)-2-oxo-1,2-dihydro-pyridin-4-ylmethyl]-3H-imidazol-4-ylmethyl}-2-methoxy-benzonitrile 4-[3-(2-Oxo-1-pyrimidin-2-yl-1,2-dihydro-pyridin-4-ylmethyl)-3H-imidazol-4-ylmethyl]-benzonitrile 4-{3-[1-(6-chloro-pyrazin-2-yl)-2-oxo-1,2-dihydro-pyridin-4-ylmethyl]-3H-imidazol-4ylmethyl}-benzonitrile 4-[3-(3'-Methyl-2-oxo-2H-[1,2']bipyridinyl-4-ylmethyl)-3H-imidazol-4-ylmethyl]-benzonitrile 4-[3-(6'-chloro-2-oxo-2H-[1,2']bipyridinyl-4-ylmethyl)-3H-imidazol-4-ylmethyl]-benzonitrile
4-[3-(6-'Triflouromethyl-2-oxo-2H-[1,2']bipyridinyl-4-ylmethyl)-3H-imidazol-4-ylmethyl]-benzonitrile
4-{3-[1-(6-Chloro-pyrimidin-2-yl)-2-oxo-1,2-dihydro-pyridin-4-ylmethyl]-3H-imidazol-4ylmethyl}-benzonitrile
4-{3-[1-(6-Chloro-pyrazin-2-yl)-2-oxo-1,2-dihydro-pyridin-4-ylmethyl]-3H-imidazol-4ylmethyl}-2-methoxy-benzonitrile
4-{3-[1-(6-Chloro-4-methyl-pyrimidin-2-yl)-2-oxo-1,2-dihydro-pyridin-4-ylmethyl]-3H-imidazol-4ylmethyl}-benzonitrile
3-[3-(6'-chloro-2-oxo-2H-[1,2']bipyridinyl-4-ylmethyl)-3H-imidazol-4-ylmethyl]-benzonitrile
4-[3-(5'-Cyano-2-oxo-2H-[1,3']bipyridinyl-4-ylmethyl)-3H-imidazol-4-ylmethyl]-benzonitrile
4-[3-(4'-Trifluoromethyl-2-oxo-2H-[1,2']bipyridinyl-4-ylmethyl)-3H-imidazol-4-ylmethyl]-benzonitrile
4-[3-(6'-Methoxy-2-oxo-2H-[1,2']bipyridinyl-4-ylmethyl)-3H-imidazol-4-ylmethyl]-benzonitrile
4-[3-(3'-Nitro-2-oxo-2H-[1,2']bipyridinyl-4-ylmethyl)-3H-imidazol-4-ylmethyl]-benzonitrile
4-[3-(3'-Trifluoromethyl-2-oxo-2H-[1,2']bipyridinyl-4-ylmethyl)-3H-imidazol-4-ylmethyl]-benzonitrile
4-{3-[1-(6-Trifluromethyl-pyrimidin-2-yl)-2-oxo-1,2-dihydro-pyridin-4-ylmethyl]-3H-imidazol-4-ylmethyl}-benzonitrile
4-[5-(4-Bromophenoxy)imidazol-1-ylmethyl]-1-(6-cyanopyrazin-2-yl)-1H-pyridin-2-one
4-{5-[1-(3-Chloro-phenyl)-2-oxo-1,2-dihydro-pyridin-4-ylmethyl]-imidazol-1-ylmethyl}-2-methoxy-benzonitrile or the pharmaceutically acceptable salts thereof.

Specific examples of the compounds of the invention are:

4-[3-(2-Oxo-1-phenyl-1,2-dihydropyridin-4-ylmethyl)-3H-imidazol-4-ylmethyl]benzonitrile

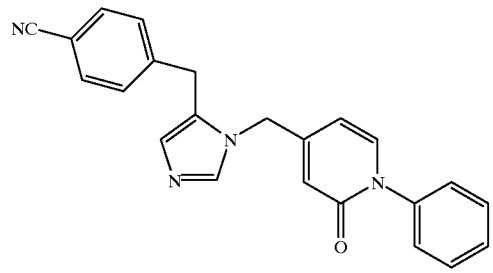

4-{3-[1-(3-Chloro-phenyl)-2-oxo-1,2-dihydropyridin-4-ylmethyl]-3H-imidazol-4-ylmethyl}benzonitrile

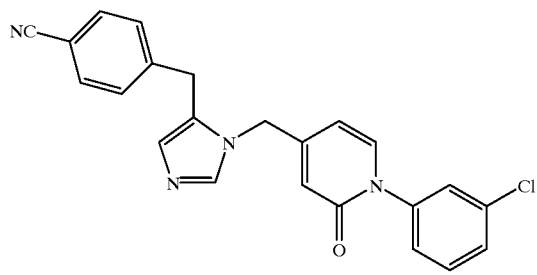

4-{5-[1-(3-Chloro-phenyl)-2-oxo-1,2-dihydro-pyridin-4-ylmethyl]-imidazol-1-ylmethyl}-2-methoxy-benzonitrile

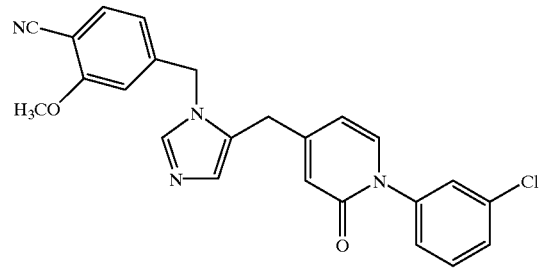

4-{3-[1-(6-Chloro-pyrimidin-2-yl)-2-oxo-1,2-dihydro-pyridin-4-ylmethyl]-3H-imidazol-4ylmethyl}-benzonitrile

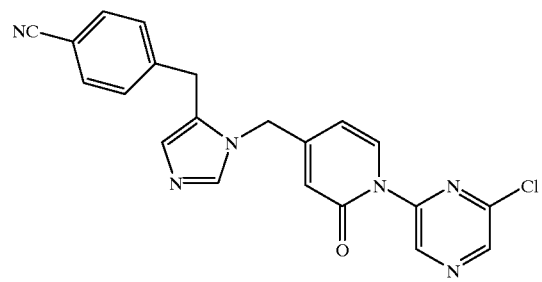

3-[3-(6'-chloro-2-oxo-2H-[1,2']bipyridinyl-4-ylmethyl)-3H-imidazol-4-ylmethyl]-benzonitrile

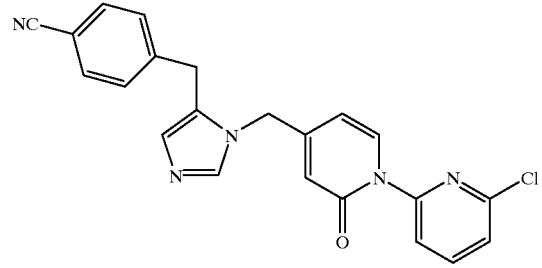

or the pharmaceutically acceptable salts thereof.

The compounds of the present invention may have asymmetric centers and occur as racemates, racemic mixtures, and as individual diastereomers, with all possible isomers, including optical isomers, being included in the present invention. When any variable (e.g. aryl, heterocycle, $R^1$, $R^2$ etc.) occurs more than one time in any constituent, its definition on each occurence is independent at every other occurence. Also, combinations of substituents and/or variables are permissible only if such combinations result in stable compounds.

As used herein, "alkyl" and the alkyl portion of aralkyl and similar terms, is intended to include both branched and straight-chain saturated aliphatic hydrocarbon groups having the specified number of carbon atoms; "alkoxy" represents an alkyl group of indicated number of carbon atoms attached through an oxygen bridge.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

"Alkynyl" groups include those groups having the specified number of carbon atoms and having one triple bonds. Examples of alkynyl groups include acetylene, 2-butynyl, 2-pentynyl, 3-pentynyl and the like.

"Halogen" or "halo" as used herein means fluoro, chloro, bromo and iodo.

As used herein, "aryl," and the aryl portion of aroyl and aralkyl, is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein in the definition of $R^3$, $R^4$, $R^5$ and $R^{6a-e}$, the term "the substituted group" is intended to mean a substituted $C_{1-8}$ alkyl, substituted $C_{2-8}$ alkenyl, substituted $C_{2-8}$ alkynyl, substituted aryl or substituted heterocycle from which the substituent(s) $R^3$, $R^4$, $R^5$ and $R^{6a-e}$ are selected.

As used herein in the definition of $R^7$, the substituted $C_{1-8}$ alkyl, substituted $C_{3-6}$ cycloalkyl, substituted aroyl, substituted aryl, substituted heteroaroyl, substituted arylsulfonyl, substituted heteroarylsulfonyl and substituted heterocycle include moieties containing from 1 to 3 substituents in addition to the point of attachment to the rest of the compound.

As used herein, when no specific substituents are set forth, the terms "substituted aryl", "substituted heterocycle" and "substituted cycloalkyl" are intended to include the cyclic group which is substituted on a substitutable ring carbon atom with 1 or 2 substitutents selected from the group which includes but is not limited to F, Cl, Br, $CF_3$, $NH_2$, $N(C_1-C_6$ alkyl$)_2$, $NO_2$, CN, $(C_1-C_6$ alkyl$)O-$, $-OH$, $(C_1-C_6$ alkyl$)S(O)_m-$, $(C_1-C_6$ alkyl$)C(O)NH-$, $H_2N-C(NH)-$, $(C_1-C_6$ alkyl$)C(O)-$, $(C_1-C_6$ alkyl$)OC(O)-$, $N_3$, $(C_1-C_6$ alkyl$)OC(O)NH-$, phenyl, pyridyl, imidazolyl, oxazolyl, isoxazolyl, thiazolyl, thienyl, furyl, isothiazolyl and $C_1-C_{20}$ alkyl.

Lines drawn into the ring systems from substituents (such as from $R^3$, $R^4$, Q etc.) means that the indicated bond may be attached to any of the substitutable ring carbon or nitrogen atoms.

The substituent illustrated by the structure

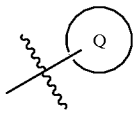

represents a 4, 5, 6 or 7 membered heterocyclic ring which comprises a nitrogen atom through which Q is attached to Y and 0–2 additional heteroatoms selected from N, S and O, and which also comprises a carbonyl, thiocarbonyl, $-C(=NR^{13})-$ or sulfonyl moiety adjacent to the nitrogen atom attached to Y and includes the following ring systems:

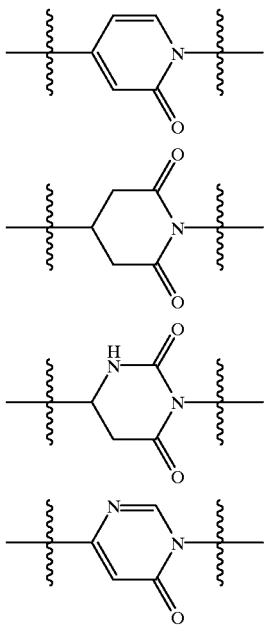

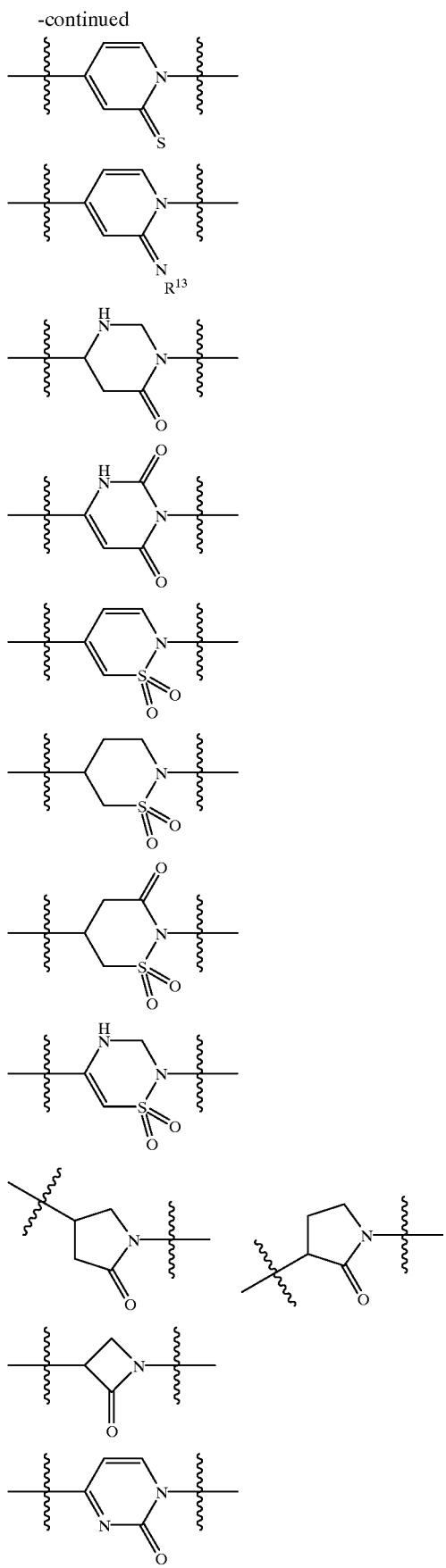
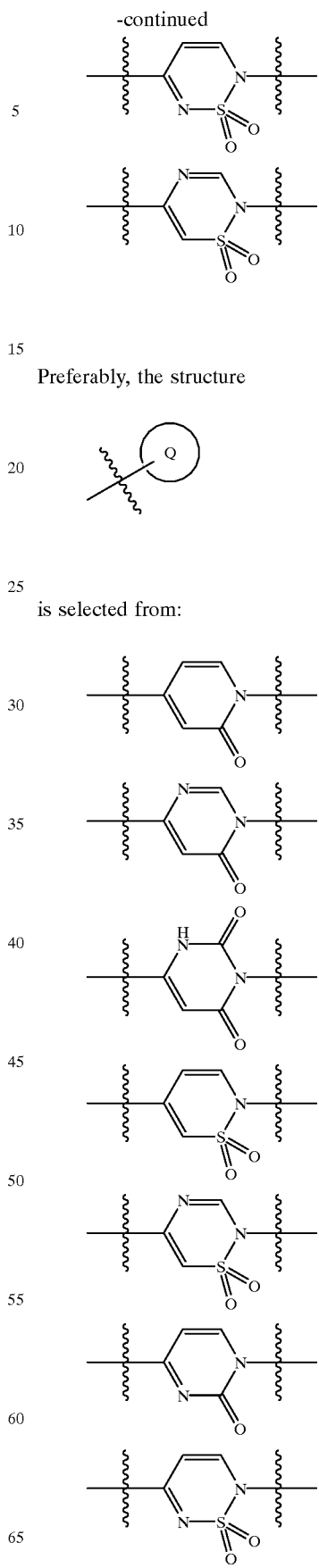
Preferably, the structure
[Q structure diagram]
is selected from:

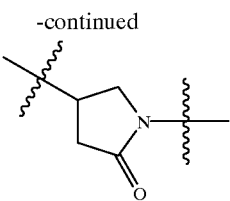

Most preferably, Q is

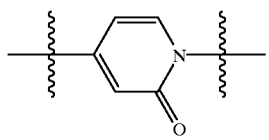

It is understood that such rings may be substituted by R³, R⁴ and/or R⁵ as defined hereinabove.

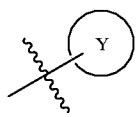

represents a 5, 6 or 7 membered carbocyclic ring wherein from 0 to 3 carbon atoms are replaced by a heteroatom selected from N, S and O, and wherein Y is attached to Q through a carbon atom and includes the following ring systems:

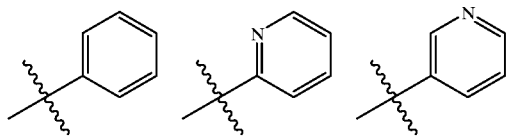

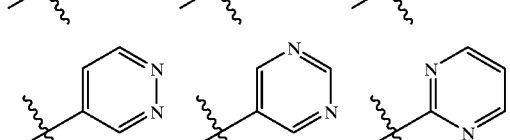

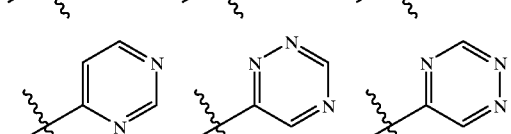

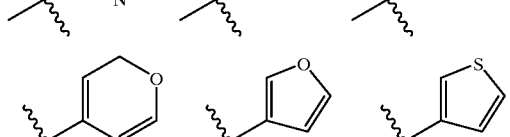

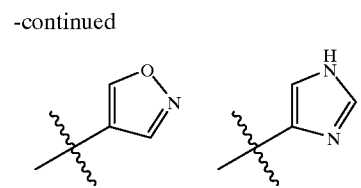

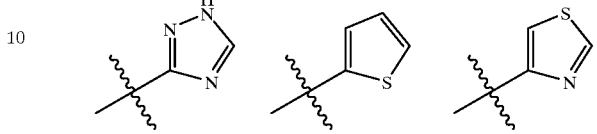

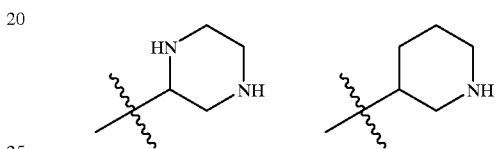

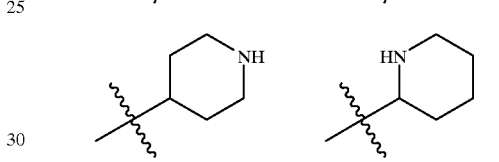

Preferably Y is the moiety designated by the following structure

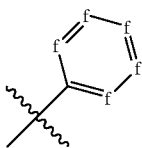

which represents an aromatic 6-membered ring and includes the following ring systems:

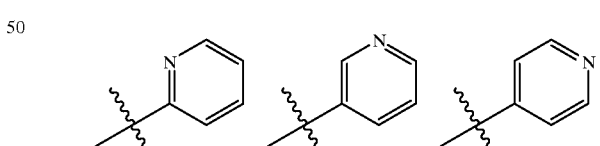

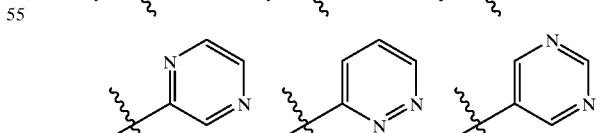

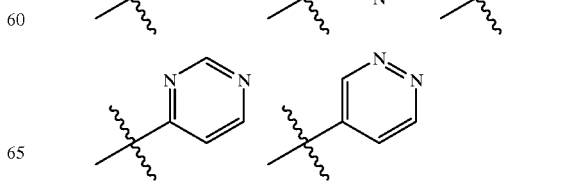

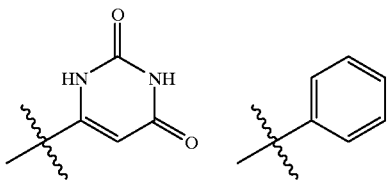

wherein it is understood that one of the ring carbon atoms is substituted with Q. Preferably, the Y is selected from phenyl and pyridyl.

The moiety described as

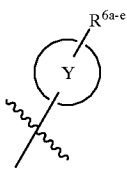

where any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH—, —(CH$_2$)$_4$— and —(CH$_2$)$_4$— includes, but is not limited to, the following structures:

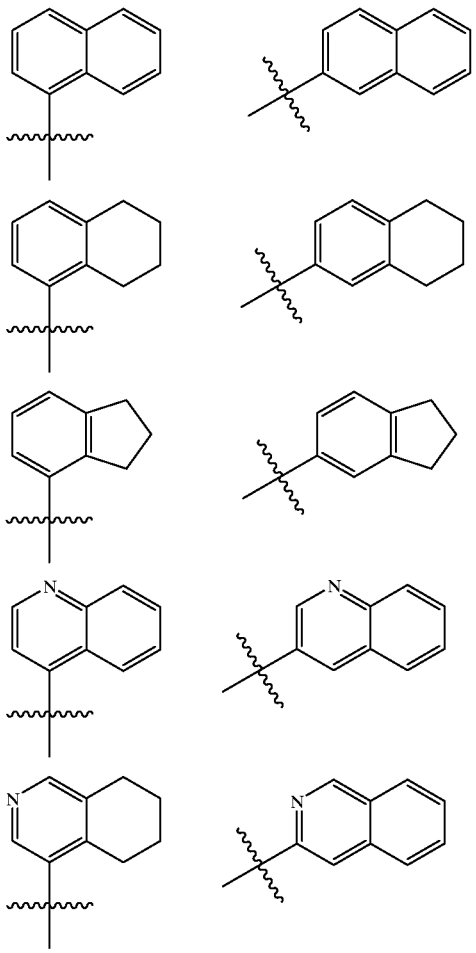

It is understood that such fused ring moieties may be further substituted by the remaining $R^{6a}$, $R^{6b}$, $R^{6c}$, $R^{6d}$ and/or $R^{6e}$ as defined hereinabove.

Preferably, $R^1$ and $R^2$ are independently selected from: hydrogen, $R^{11}C(O)O$—, —$N(R^{10})_2$, $R^{10}C(O)NR^{10}O$—, $R^{10}O$— or unsubstituted or substituted $C_1$–$C_6$ alkyl wherein the substituent on the substituted $C_1$–$C_6$ alkyl is selected from unsubstituted or substituted phenyl, —$N(R^{10})_2$, $R^{10}O$— and $R^{10}C(O)NR^{10}$—.

Preferably, $R^3$ is selected from:

a) hydrogen,
b) $C_3$–$C_{10}$ cycloalkyl, halogen, $C_1$–$C_6$ perfluoroalkyl, $R^{12}O$—, CN, NO$_2$, $R^{10}C(O)$— or —$N(R^{10})_2$,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2$ NC(O)—, $R^{10}_2N$—C(NR$^{10}$)—, CN, $R^{10}C(O)$—, N$_3$, —N(R$^{10}$)$_2$, and $R^{11}OC(O)$—NR$^{10}$—.

Preferably, $R^4$ is selected from: hydrogen, halogen, trifluoromethyl, trifluoromethoxy and $C_1$–$C_6$ alkyl.

Preferably, $R^5$ is hydrogen.

Preferably, $R^{6a}$, $R^{6b}$, $R^{6c}$, $R^{6d}$ and $R^{6e}$ are independently selected from:

a) hydrogen,
b) $C_3$–$C_{10}$ cycloalkyl, halogen, $C_1$–$C_6$ perfluoroalkyl, $R^{12}O$—, $R^{11}S(O)_m$—, CN, NO$_2$, $R^{10}C(O)$— or —$N(R^{10})_2$,
c) unsubstituted $C_1$–$C_6$ alkyl; and
d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $R^{12}O$—, $R^{11}S(O)_m$—, $R^{10}C(O)$— or —$N(R^{10})_2$.

Preferably, $R^8$ is independently selected from:

a) hydrogen, and
b) aryl, substituted aryl, heterocycle, substituted heterocycle, $C_1$–$C_6$ perfluoroalkyl, $R^{10}O$— or CN.

Preferably, $R^9$ is hydrogen, halogen or methyl.

Preferably, $R^{10}$ is independently selected from hydrogen, $C_1$–$C_6$ alkyl, benzyl, 2,2,2-trifluoroethyl, aryl and substituted aryl. More preferably, $R^{10}$ is selected from H, $C_1$–$C_6$ alkyl and benzyl.

Preferably, $A^1$ and $A^2$ are independently selected from: a bond, —C(O)NR$^{10}$—, —NR$^{10}$C(O)—, O, —N(R$^{10}$)—, —S(O)$_2$N(R$^{10}$)— and —N(R$^{10}$)S(O)$_2$—.

Preferably, V is selected from hydrogen, heterocycle and aryl. More preferably, V is phenyl and pyridyl.

Preferably, W is selected from imidazolinyl, imidazolyl, oxazolyl, pyrazolyl, pyyrolidinyl, thiazolyl and pyridyl. More preferably, W is selected from imidazolyl and pyridyl.

Preferably, n and r are independently 0, 1, or 2.
Preferably s is 0.
Preferably t is 1.
Preferably, the moiety

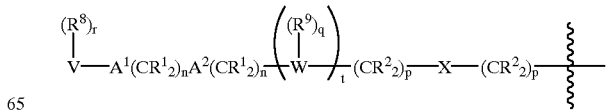

is selected from:

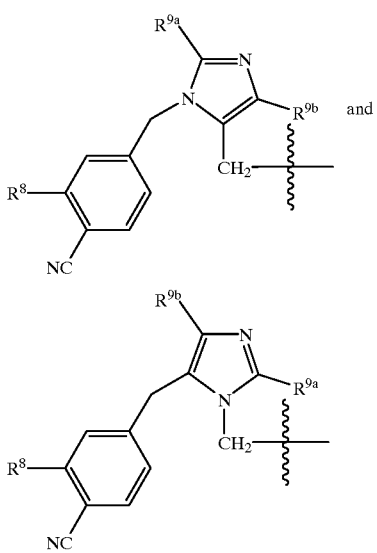

It is intended that the definition of any substituent or variable (e.g., $R^1$, $R^2$, $R^9$, n, etc.) at a particular location in a molecule be independent of its definitions elsewhere in that molecule. Thus, —N($R^{10}$)$_2$ represents —NHH, —NHCH$_3$, —NHC$_2$H$_5$, etc. It is understood that substituents and substitution patterns on the compounds of the instant invention can be selected by one of ordinary skill in the art to provide compounds that are chemically stable and that can be synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, palmoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Schemes 1–17, in addition to other standard manipulations such as ester hydrolysis, cleavage of protecting groups, etc., as may be known in the literature or exemplified in the experimental procedures. Substituents $R^3$, $R^6$ and $R^8$, as shown in the Schemes, represent the substituents $R^3$, $R^4$, $R^5$, $R^{6a}$, $R^{6b}$, $R^{6c}$, $R^{6d}$, $R^{6e}$ and $R^8$; although only one such $R^3$, $R^6$ or $R^8$ is present in the intermediates and products of the schemes, it is understood that the reactions shown are also applicable when such aryl or heterocyclic moieties contain multiple substituents.

These reactions may be employed in a linear sequence to provide the compounds of the invention or they may be used to synthesize fragments which are subsequently joined by the alkylation reactions described in the Schemes. The reactions described in the Schemes are illustrative only and are not meant to be limiting. Other reactions useful in the preparation of heteroaryl moieties are described in "Comprehensive Organic Chemistry, Volume 4: Heterocyclic Compounds" ed. P. G. Sammes, Oxford (1979) and references therein.

Synopsis of Schemes 1–17:

The requisite intermediates are in some cases commercially available, or can be prepared according to literature procedures. Schemes 1–8 illustrate synthesis of the instant bicyclic compounds which incorporate a preferred benzylimidazolyl sidechain. Thus, in Scheme 1, for example, a bicyclic intermediate that is not commercially available may be synthesized by methods known in the art. Thus, a suitably substituted pyridinonyl alcohol 2 may be synthesized starting from the corresponding isonicotinate 1 according to procedures described by Boekelhiede and Lehn (*J. Org. Chem.*, 26:428–430 (1961)). The alcohol is then protected and reacted under Ullmann coupling conditions with a suitably substituted phenyl iodide, to provide the intermediate bicyclic alcohol 3. The intermediate alcohol 3 may converted to the corresponding bromide 4. The bromide 4 may be coupled to a suitably substituted benzylimidazolyl 5 to provide, after deprotection, the instant compound 6.

Schemes 2–4 illustrate methods of synthesizing related or alcohol intermediates, which can then be processed as described in Scheme 1. Thus, Scheme 2 illustrates preparation of a pyridyl-pyridinonyl alcohol and thienylpyridinonyl alcohol starting with the suitably substituted halogenated heterocycles.

Scheme 3 illustrates preparation of the intermediate bromide 9 wherein the preferred pyridinone is replaced by a saturated lactam. Acylation of a suitably substituted aniline 7 with a suitably substituted brominated acyl chloride provides the acylated intermediate 8. Closure of the lactam ring provides the intermediate alcohol, which is converted to the bromide as described above.

Scheme 4 illustrates synthesis of an instant compound wherein a non-hydrogen $R^{9b}$ is incorporated in the instant compound. Thus, a readily available 4-substituted imidazole 10 may be selectively iodinated to provide the 5-iodoimidazole 11. That imidazole 11 may then be protected and coupled to a suitably substituted benzyl moiety to provide intermediate 12. Intermediate 12 can then undergo the alkylation reactions that were described hereinabove.

Scheme 5 illustrates synthesis of instant compounds that incorporate a preferred imidazolyl moiety connected to the biaryl via an alkyl amino, sulfonamide or amide linker. Thus, the 4-aminoalkylimidazole 13, wherein the primary amine is protected as the phthalimide, is selectively alkylated then deprotected to provide the amine 14. The amine 14 may then react under conditions well known in the art with various activated arylheteroaryl moieties to provide the instant compounds shown.

Compounds of the instant invention wherein the $A^1(CR^1_2)_nA^2(CR^1_2)_n$ linker is oxygen may be synthesized by methods known in the art, for example as shown in Scheme 6. The suitably substituted phenol 15 may be reacted with methyl N-(cyano)$_m$ethanimidate to provide the 4-phenoxyimidazole 16. After selective protection of one of the imidazolyl nitrogens, the intermediate 17 can undergo alkylation reactions as described for the benzylimidazoles hereinabove.

Compounds of the instant invention wherein the $A^1(CR^1_2)_nA^2(CR^1_2)_n$ linker is a substituted methylene may be synthesized by the methods shown in Scheme 7. Thus, the N-protected imidazolyl iodide 18 is reacted, under Grignard conditions with a suitably protected benzaldehyde to provide the alcohol 19. Acylation, followed by the alkylation procedure illustrated in the Schemes above (in particular, Scheme 1) provides the instant compound 20. If other $R^1$ substituents are desired, the acetyl moiety can be manipulated as illustrated in the Scheme.

Scheme 8 illustrates incorporation of an acetyl moiety as the $(CR^2_2)_pX(CR^2_2)_p$ linker of the instant compounds. Thus, the suitably substituted acetyl pyridine 21 is converted to the corresponding pyridinone and undergoes the Ullmann reaction with a suitably substituted phenyl iodide. The acetyl is then brominated to provide intermediate 22. Reaction with the imidazolyl reagent 5 provides, after deprotection, the instant compound 23.

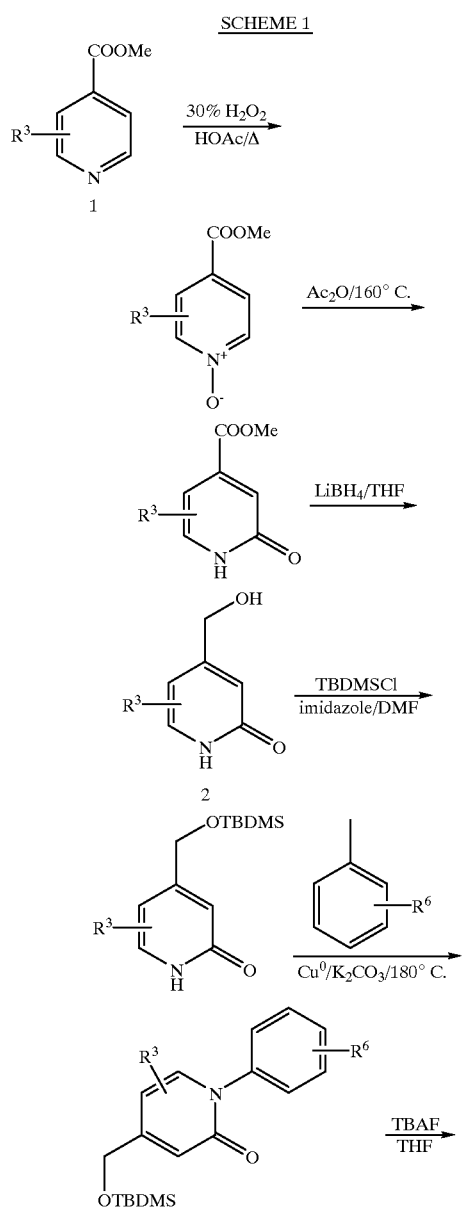

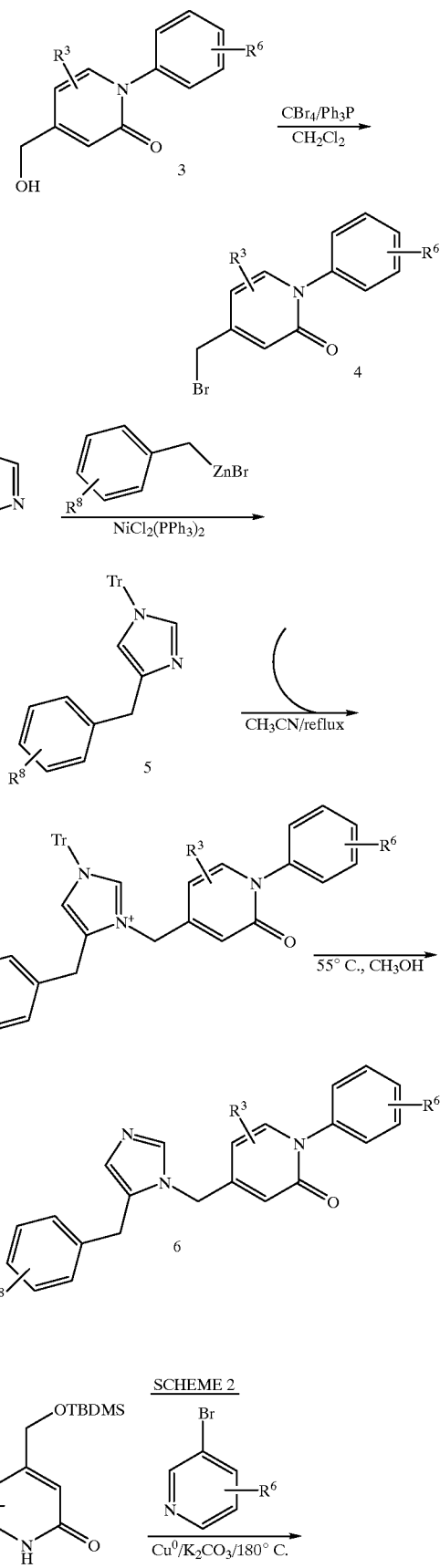

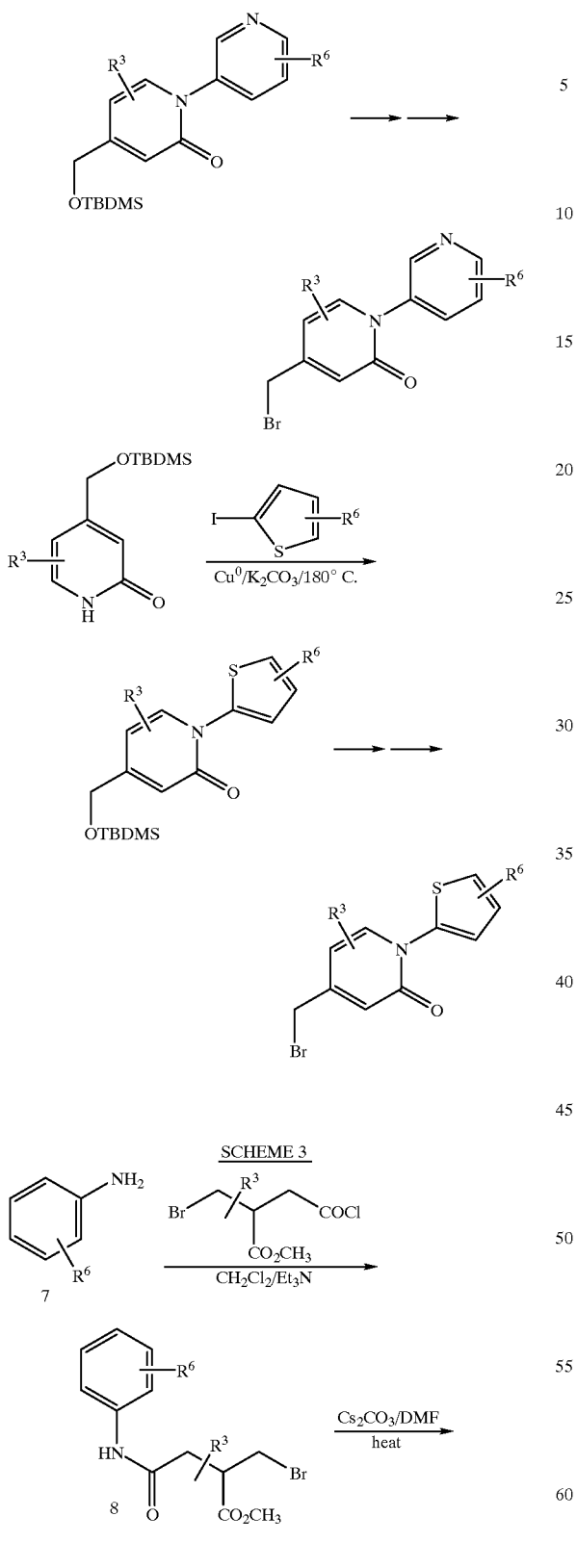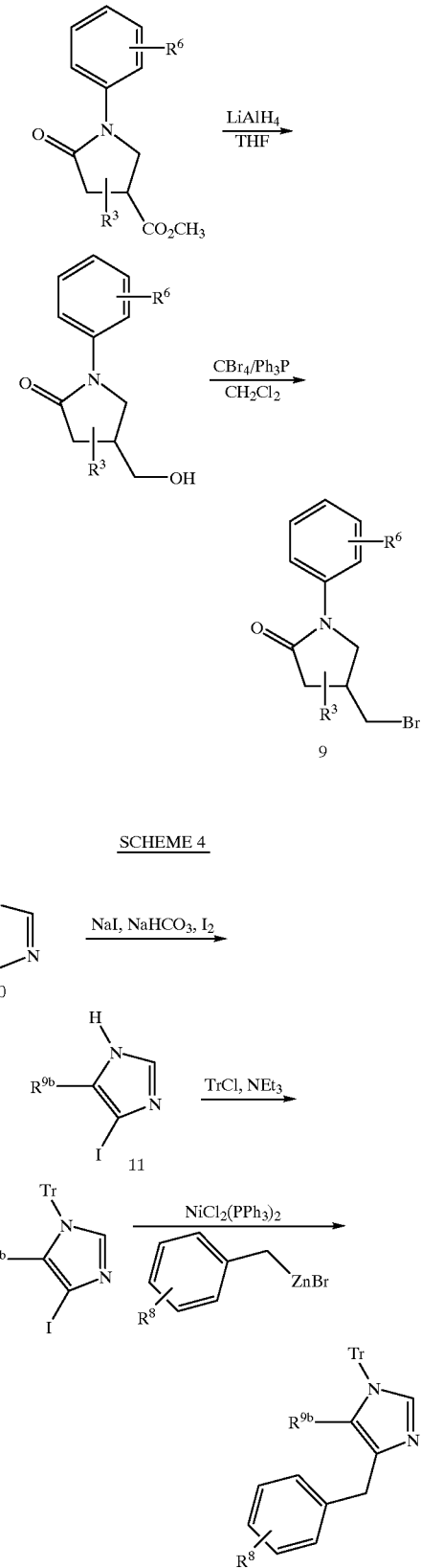

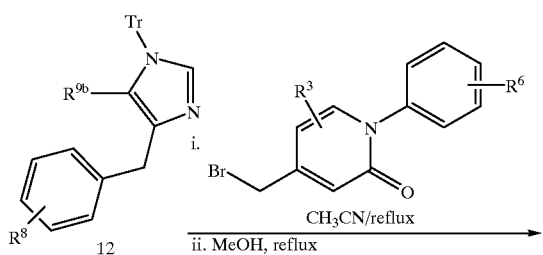
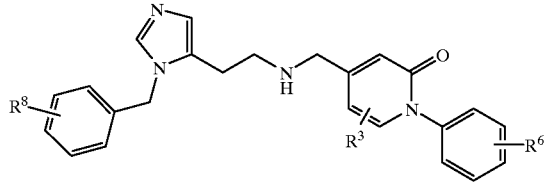
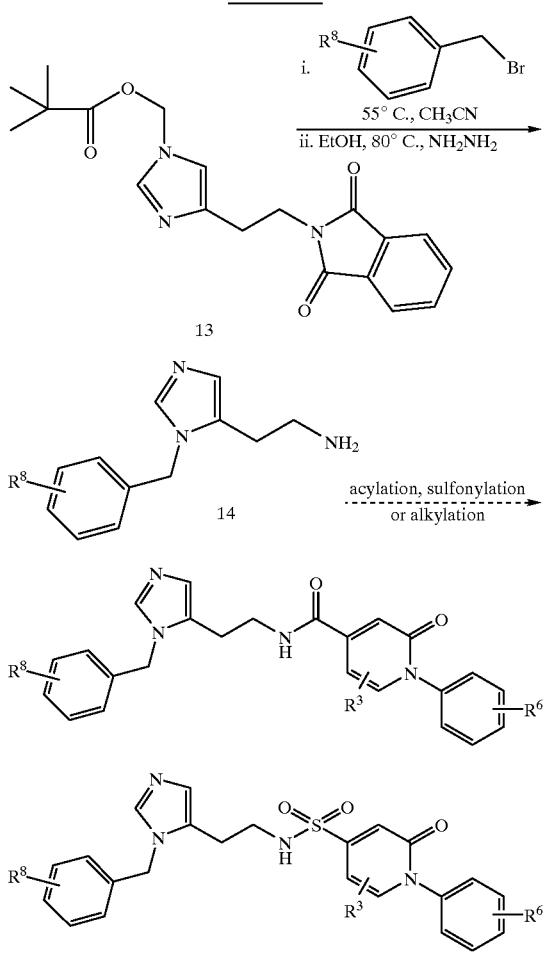
SCHEME 5
SCHEME 6
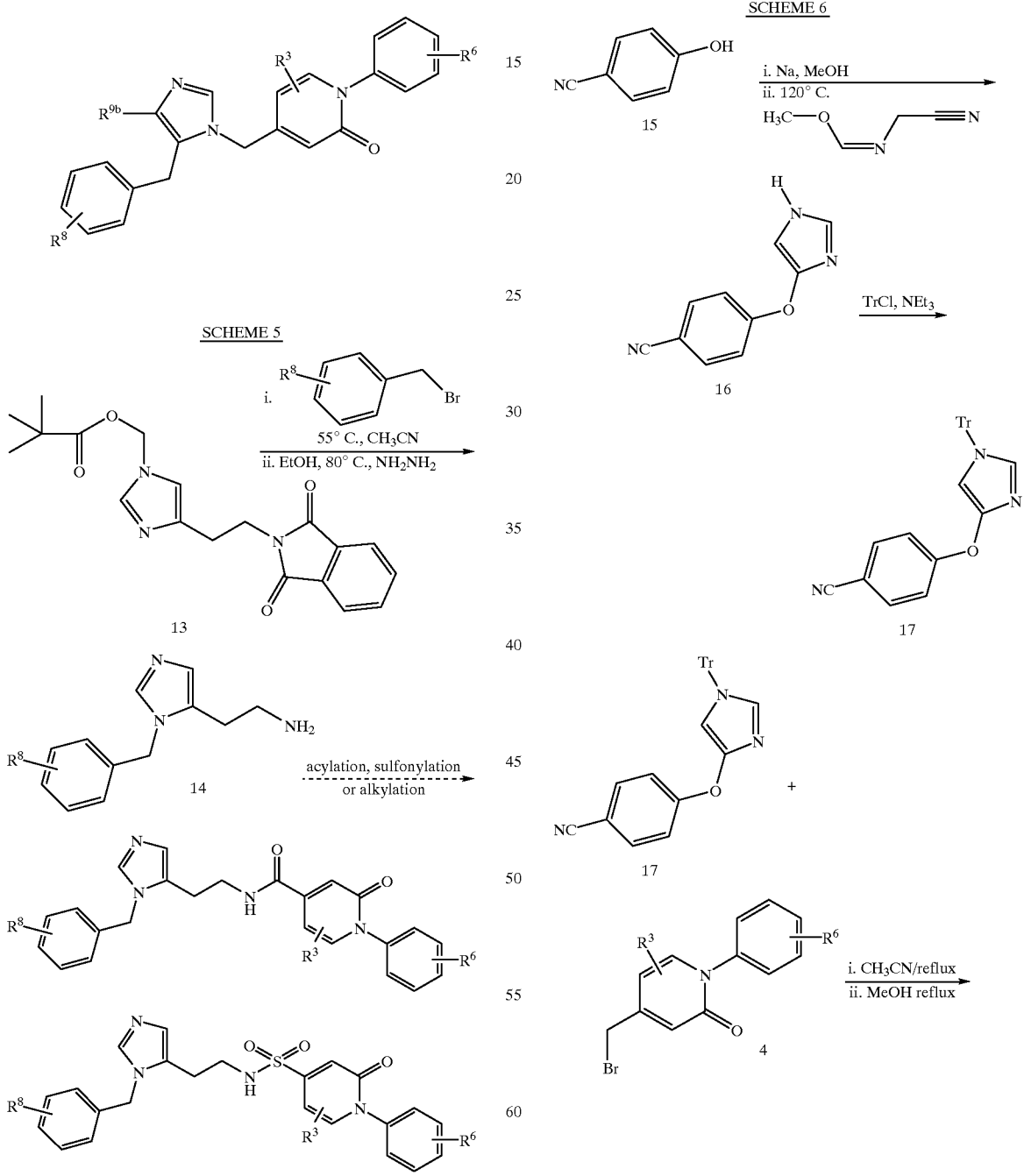

41
-continued
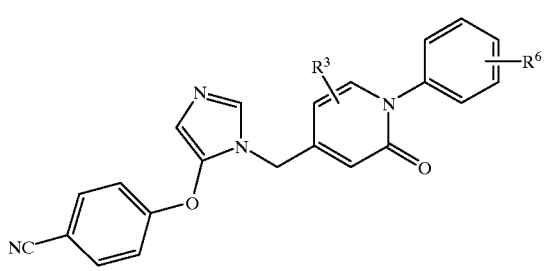
42
-continued
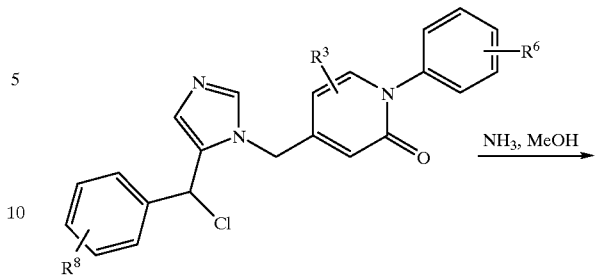
NH₃, MeOH
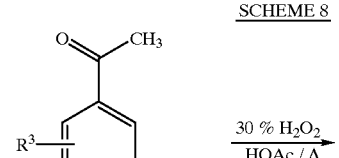
+
SCHEME 7
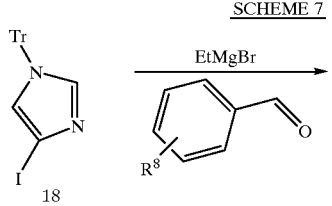
EtMgBr
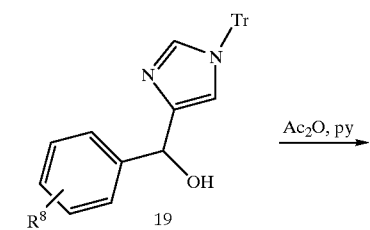
Ac₂O, py
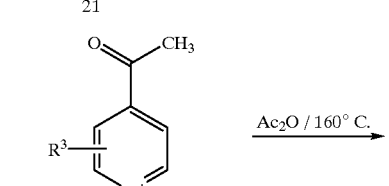
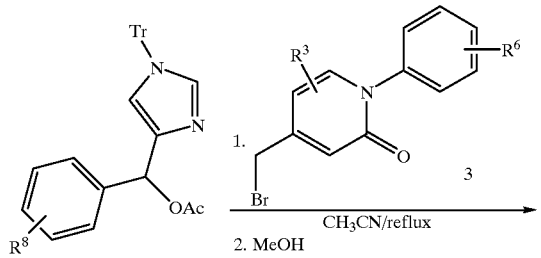
1.  <image of 3> Br / CH₃CN/reflux
2. MeOH
SCHEME 8
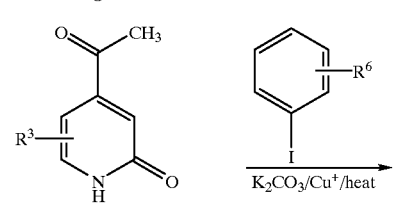
30 % H₂O₂ / HOAc / Δ
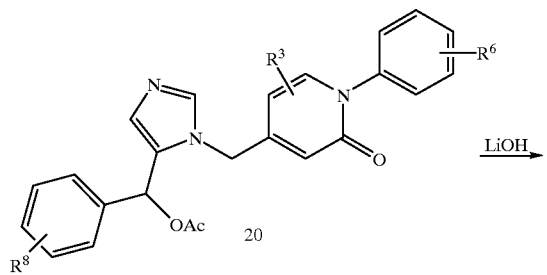
LiOH
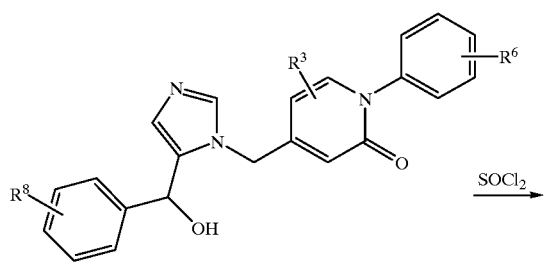
SOCl₂
Ac₂O / 160° C.
K₂CO₃/Cu⁺/heat

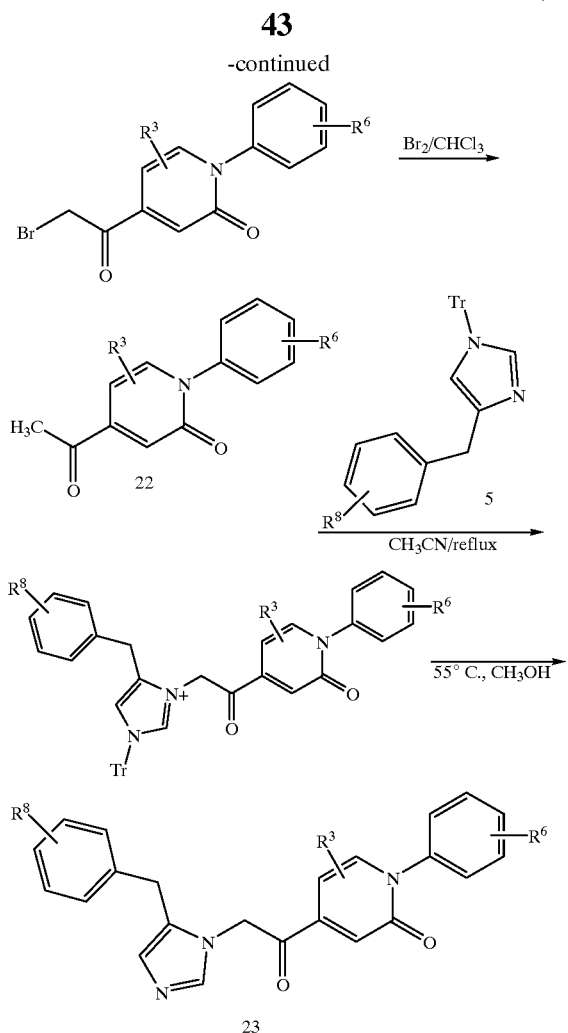

Schemes 9–17 illustrate reactions wherein the moiety

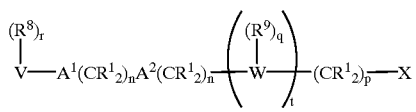

incorporated in the compounds of the instant invention is represented by other than a substituted imidazole-containing group.

Thus, the intermediates whose synthesis are illustrated in the Schemes, and other pyridinonecarbocyclic and pyridinoneheterocyclic intermediates obtained commercially or readily synthesized, can be coupled with a variety of aldehydes. The aldehydes can be prepared by standard procedures, such as that described by O. P. Goel, U. Krolls, M. Stier and S. Kesten in *Organic Syntheses*, 1988, 67, 69–75, from the appropriate amino acid. Knochel chemistry may be utilized, as shown in Scheme 9, to incorporate the arylpyridinone moiety. Thus, a suitably substituted 4-(bromo)pyridine is converted to the corresponding pyridinone 24 as described above and the pyridinone is coupled to a suitably substituted phenyl iodide as previously described above. The resulting bromide 25 is treated with zinc(0) and the resulting zinc bromide reagent 26 is reacted with an aldehyde to provide the C-alkylated instant compound 27. Compound 27 can be deoxygenated by methods known in the art, such as a catalytic hydrogention, then deprotected with trifluoroacetic acid in methylene chloride to give the final compound 28. The compound 28 may be isolated in the salt form, for example, as a trifluoroacetate, hydrochloride or acetate salt, among others. The product diamine 28 can further be selectively protected to obtain 29, which can subsequently be reductively alkylated with a second aldehyde to obtain compound 30. Removal of the protecting group, and conversion to cyclized products such as the dihydroimidazole 31 can be accomplished by literature procedures.

If the arylpyridinone zinc bromide reagent is reacted with an aldehyde which also has a protected hydroxyl group, such as 32 in Scheme 10, the protecting groups can be subsequently removed to unmask the hydroxyl group (Schemes 10, 11). The alcohol can be oxidized under standard conditions to e.g. an aldehyde, which can then be reacted with a variety of organometallic reagents such as alkyl lithium reagents, to obtain secondary alcohols such as 34. In addition, the fully deprotected amino alcohol 35 can be reductively alkylated (under conditions described previously) with a variety of aldehydes to obtain secondary amines, such as 36 (Scheme 11), or tertiary amines.

The Boc protected amino alcohol 33 can also be utilized to synthesize 2-aziridinylmethylarylheteroaryl such as 37 (Scheme 12). Treating 33 with 1,1'-sulfonyldiimidazole and sodium hydride in a solvent such as dimethylformamide led to the formation of aziridine 37. The aziridine is reacted with a nucleophile, such as a thiol, in the presence of base to yield the ring-opened product 38.

In addition, the arylpyridinone reagent can be reacted with aldehydes derived from amino acids such as O-alkylated tyrosines, according to standard procedures, to obtain compounds such as 40, as shown in Scheme 13. When R' is an aryl group, 40 can first be hydrogenated to unmask the phenol, and the amine group deprotected with acid to produce 41. Alternatively, the amine protecting group in 40 can be removed, and O-alkylated phenolic amines such as 42 produced.

Schemes 14–17 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.

SCHEME 9
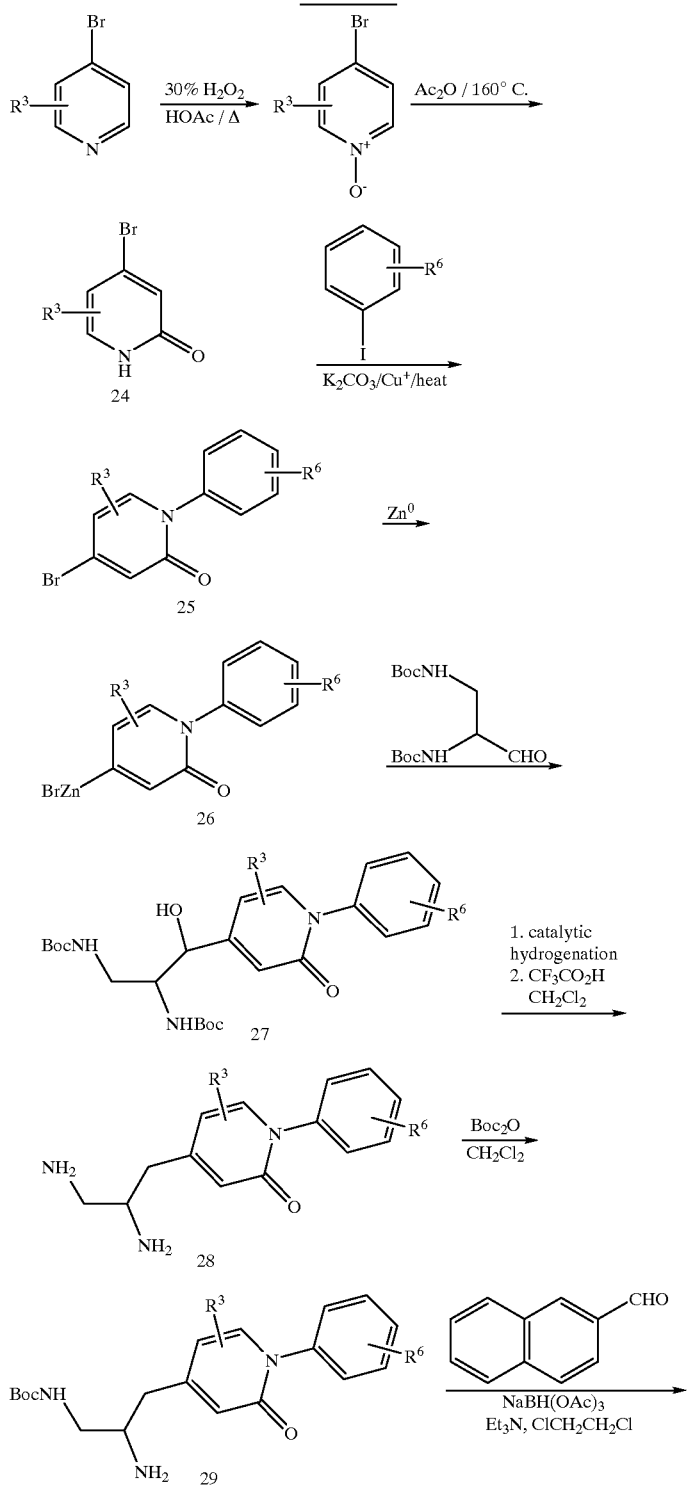

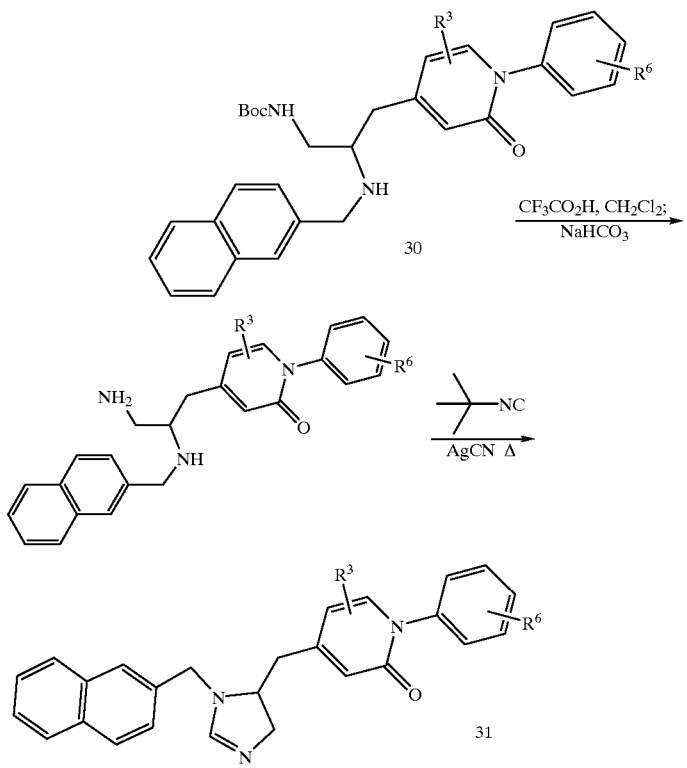
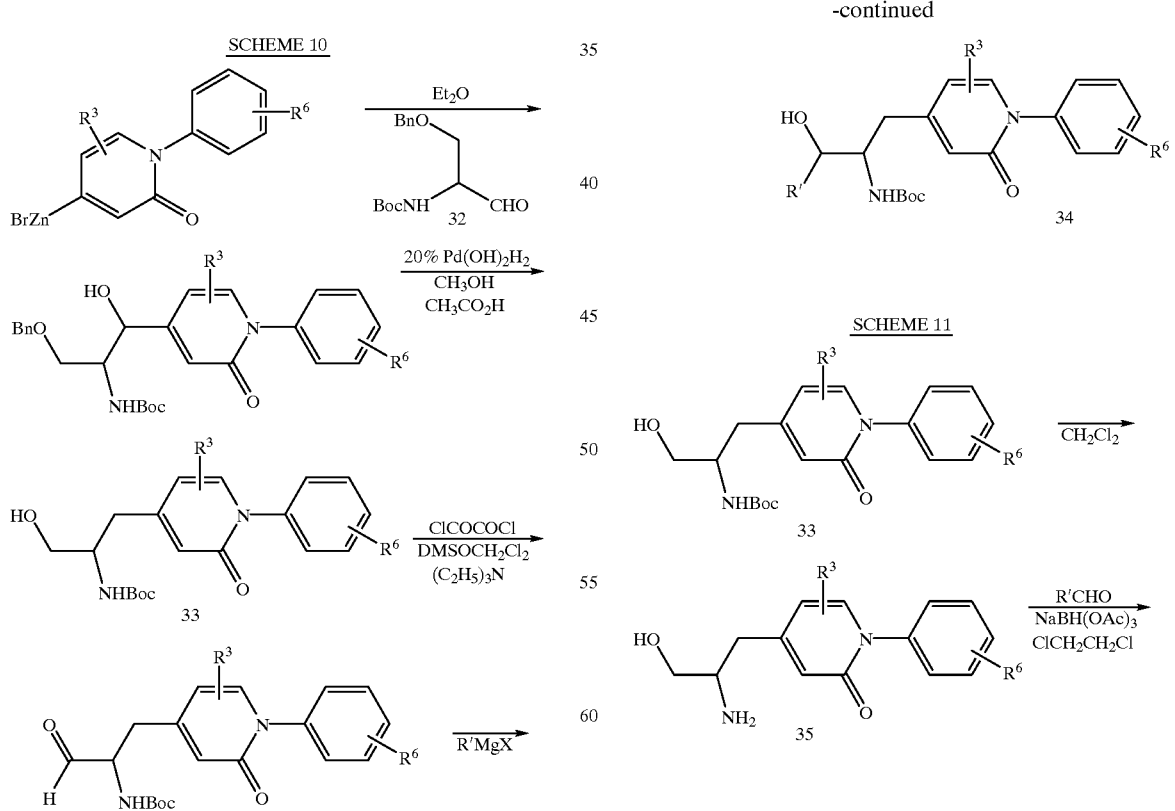

49
-continued
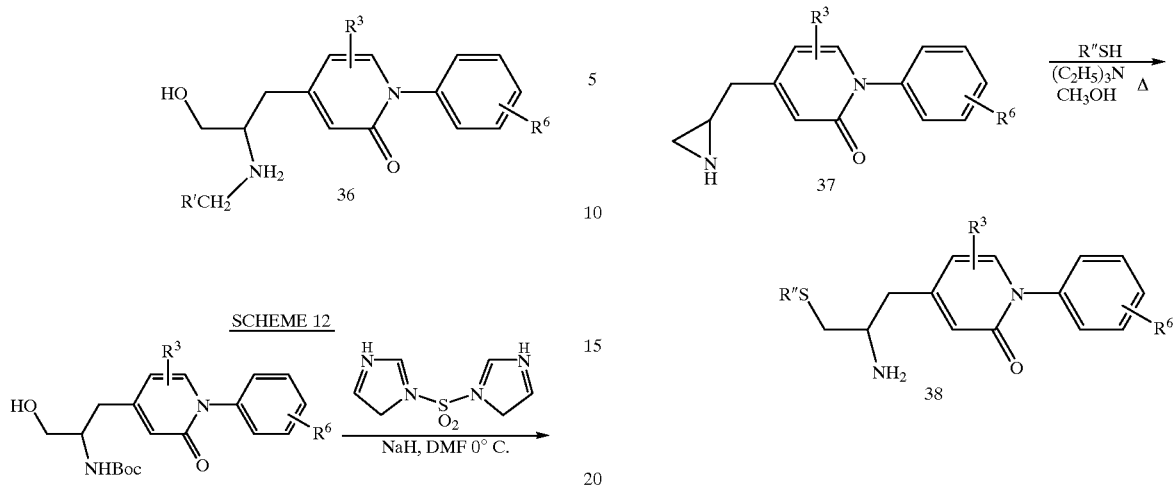
50
-continued
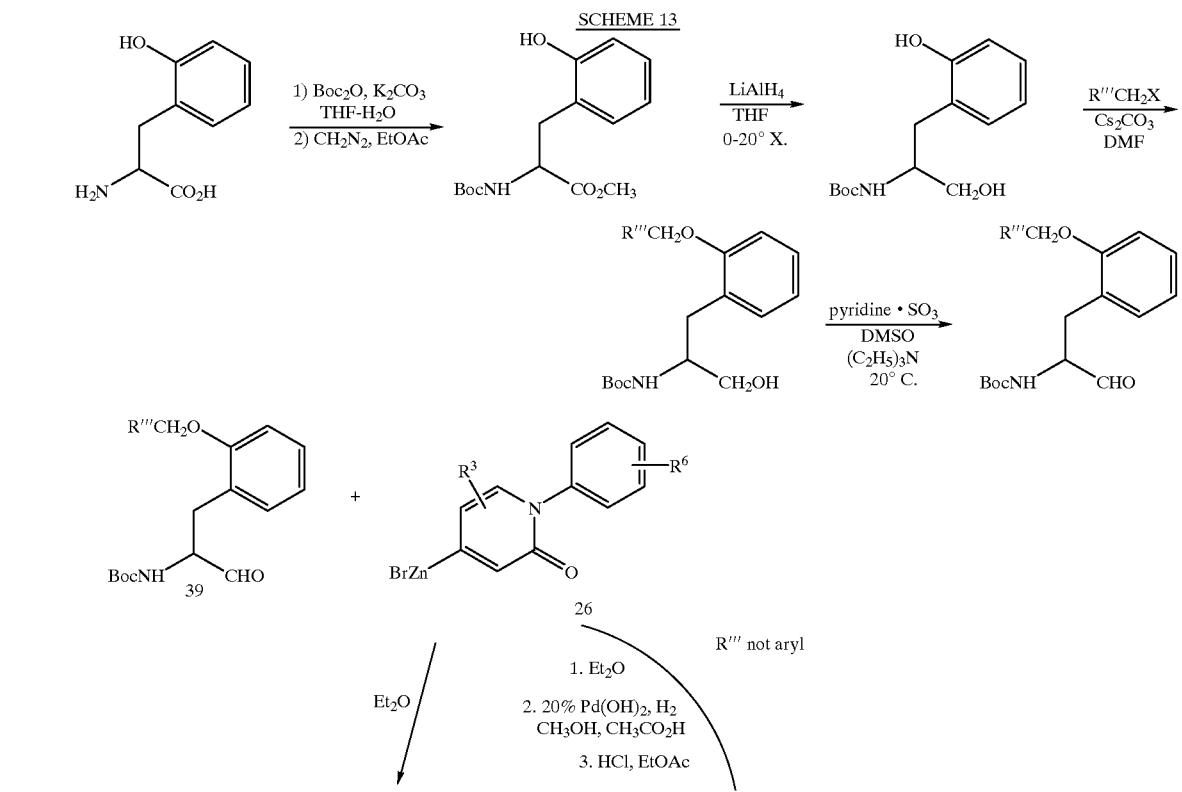

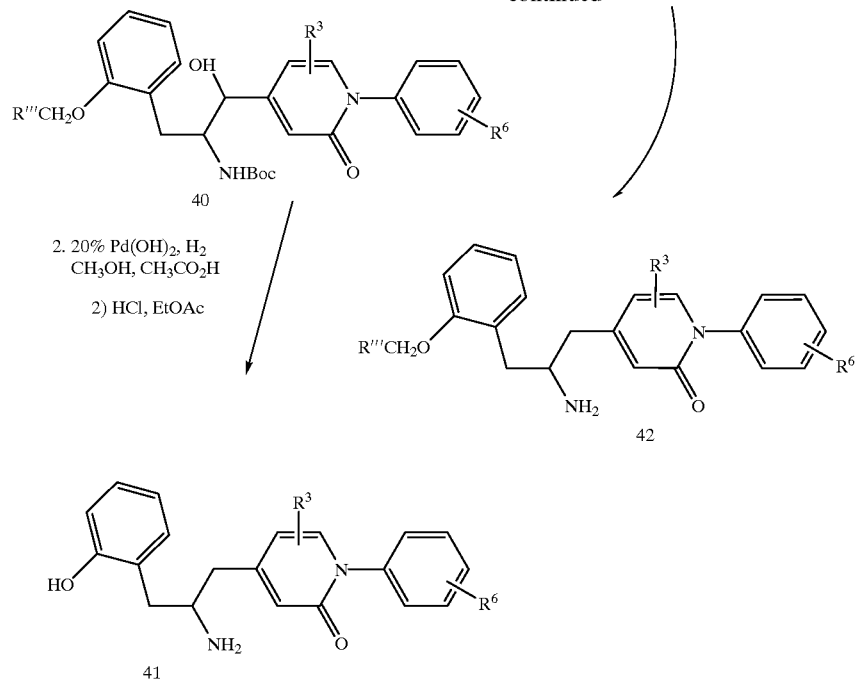
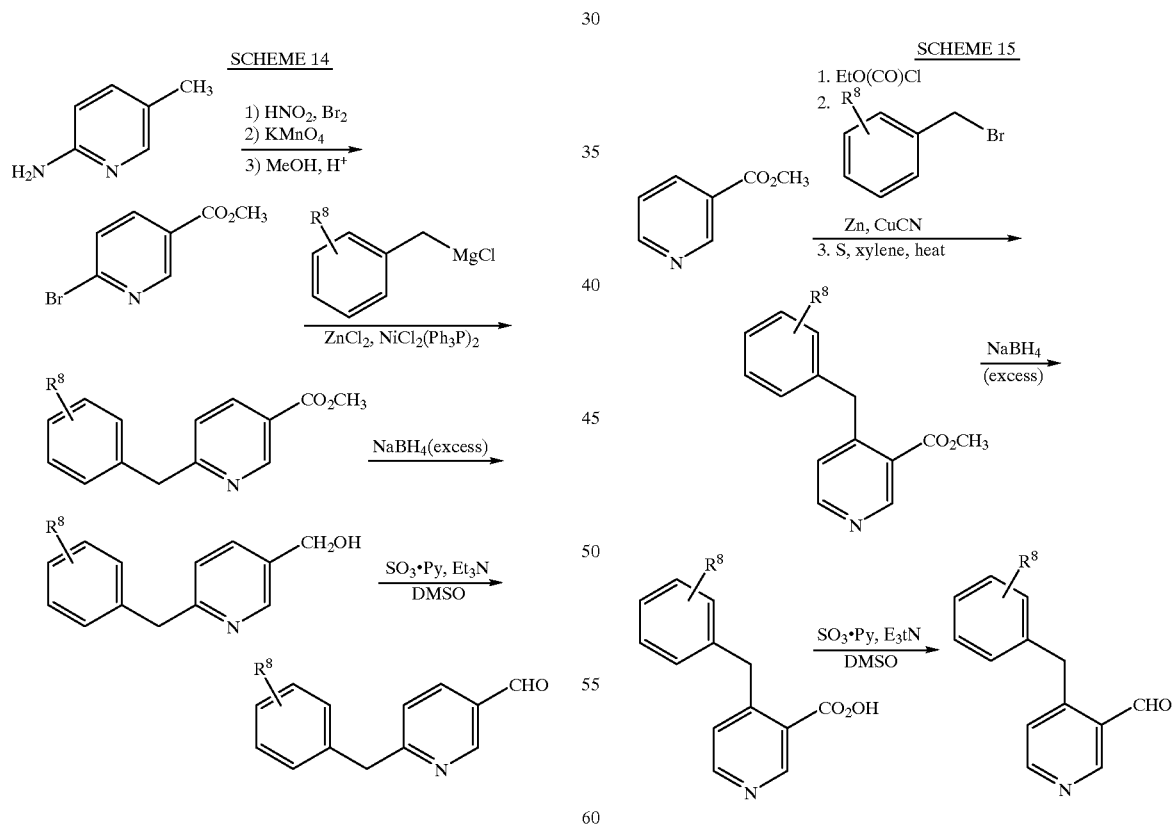
SCHEME 14
SCHEME 15

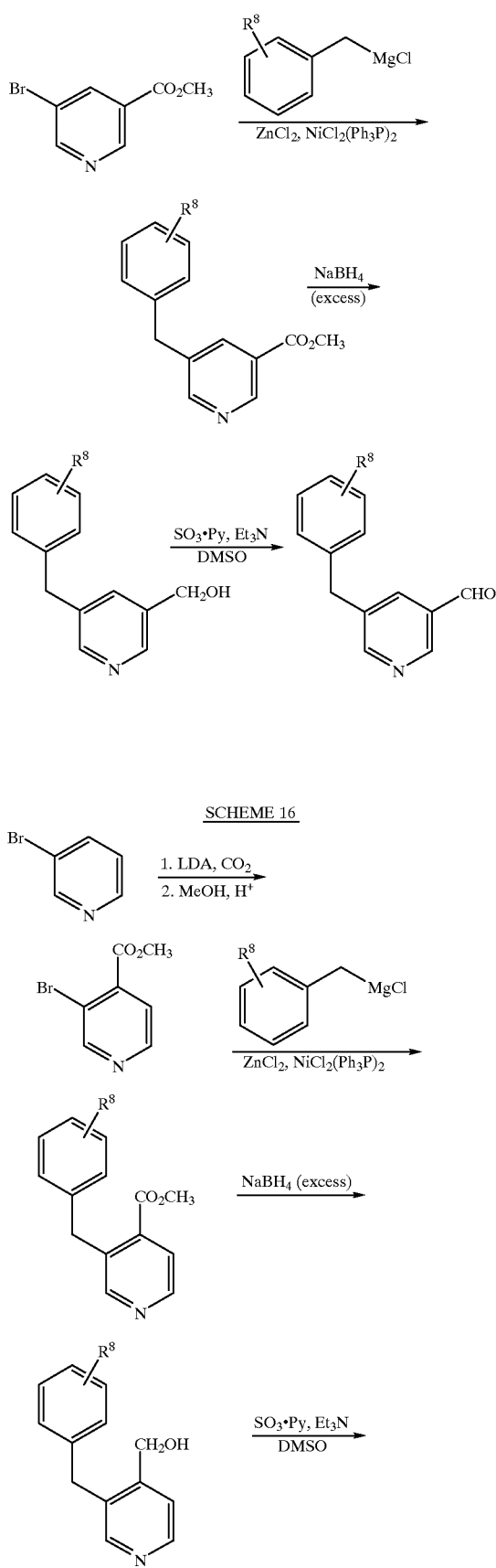

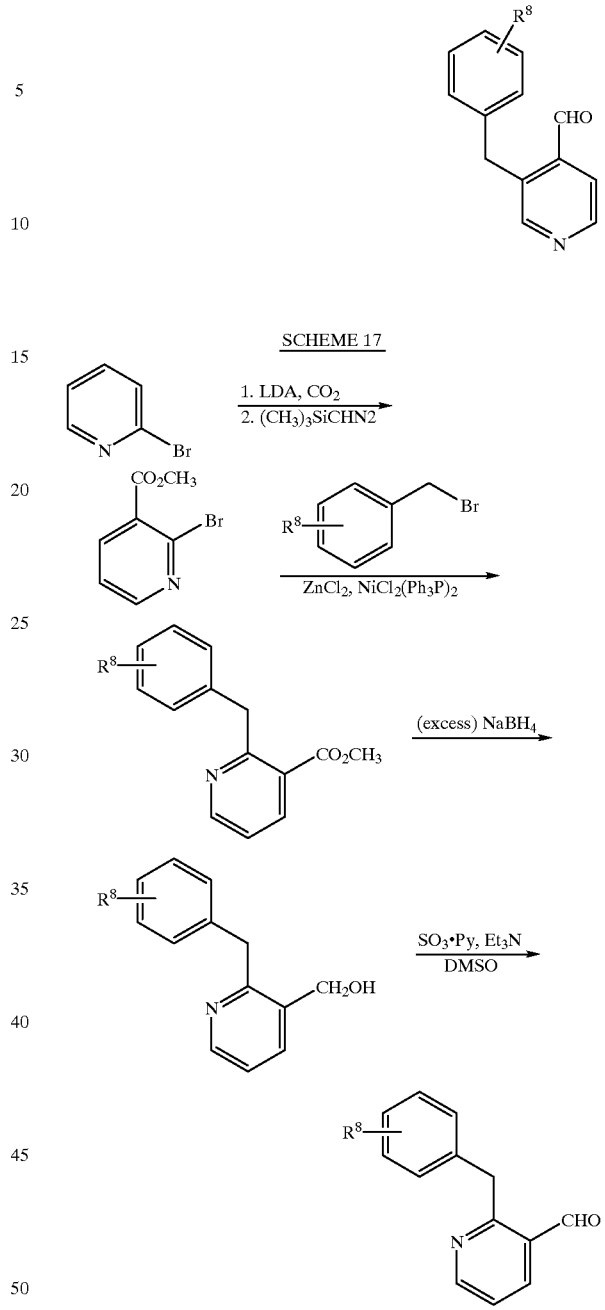

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scr, abl, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research*, 55: 4575–4580 (1995)). Such anti-angiogenesis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science*, 256:1331–1333 (1992).

The compounds of this instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. *American Journal of Pathology*, 142:1051–1060 (1993) and B. Cowley, Jr. et al.*FASEB Journal*, 2:A3160 (1988)).

The instant compounds may also be useful for the treatment of fungal infections.

The instant compounds may also be useful as inhibitors of proliferation of vascular smooth muscle cells and therefore useful in the prevention and therapy of arteriosclerosis and diabetic disturbance of blood vessels.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the instant invention may also be coadministered with other well known therapeutic agents that are selected for their particular usefulness against the condition that is being treated. For example, the instant compounds may be useful in combination with known anti-cancer and cytotoxic agents. Similarly, the instant compounds may be useful in combination with agents that are effective in the treatment and prevention of NF-1, restinosis, polycystic kidney disease, infections of hepatitis delta and related viruses and fungal infections. The instant compounds may also be useful in combination with other inhibitors of parts of the signalling pathway that links cell surface growth factor receptors to nuclear signals initiating cellular proliferation. Thus, the instant compounds may be utilized in combination with farnesyl pyrophosphate competitive inhibitors of the activity of farnesyl-protein transferase or in combination with a compound which has Raf antagonist activity.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's blood-stream by local bolus injection.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

EXAMPLE 1

4-[3-(2-Oxo-1-phenyl-1,2-dihydropyridin-4-ylmethyl)-3H-imidazol-4-ylmethyl]benzonitrile Step 1: 4-Hydroxymethyl-1H-pyridin-2-one 2-Oxo-1,2-dihydropyridine-4-carboxylic acid methyl ester (1.8 g, 12.2 mmol), prepared as described in *J. Org. Chem.*, 26, 428 (1961), was suspended in THF(100 ml). A small amount of DMF was added to help increase solubility. $LiBH_4$ (61 mmol) was added and the reaction was stirred for 18 hours at room temperature. MeOH and $H_2O$ are added to quench the reaction. The reaction is then concentrated to yield a yellow oil. Flash chromatography (5% MeOH/$CHCl_3$ to 20% MeOH/$CHCl_3$) yielded 4-hydroxymethyl-1H-pyridin-2-one as a white solid.

$^1$H NMR (400 MHz, $CD_3OD$) δ 7.38–7.36 (1H,d); 6.56 (s, 1H); 6.37–6.36 (d, 1H); 4.50 s, 2H).

Step 2: 4-(tert-butyldimethylsilyloxymethyl)-1H-pyridin-2-one

4-Hydroxymethyl-1H-pyridin-2-one from Step 1 (1.3 g, 10.5 mmol) was dissolved in DMF. t-Butyl dimethylsilyl chloride (12.6 mmol, 1.9 g) and imidazole (12.6 mmol, 858 mg) were added and the reaction was stirred for 16 hours. The reaction mixture was diluted with EtOAc and washed with $H_2O$ (2x) and brine. The organic layer was dried ($MgSO_4$), filtered and concentrated to yield a yellow oil Flash chromatography (EtOAC) yielded 4-(tert-butyldimethylsilyloxy-methyl)-1H-pyridin-2-one as an off white solid.

$^1$H NMR (400 MHz, $CDCl_3$) δ 7.30–7.28 (d, 1H); 6.60 (s, 1H); 6.20–6.18 (d, 1H); 4.58 (s, 2H); 0.955 (s, 9H); 0.11 (s, 6H).

Step 3: 4-(tert-butyl-dimethyl-silanyloxymethyl)-1-phenyl-1H-pyridin-2-one 4-(Tert-butyldimethylsilyloxymethyl)-1H-pyridin-2-one from Step 2 (1.5 g, 6.3 mmol) was dissolved in iodobenzene (189 mmol, 21.12 mL) and treated with copper (6.3 mmol, 400 mg) and $K_2CO_3$ (6.93 mmol, 958 mg.). The brown slurry was heated to 180° for 16 hrs. The reaction mixture was cooled, diluted with $CHCl_3$ and washed with saturated $NaHCO_3$. The aqueous layer was back extracted with $CHCl_3$ (2x). The organic layers were combined, washed with brine, dried ($MgSO_4$), filtered and concentrated to yield a yellow oil. Flash Chromatography (20% EtOAc/Hexane) yielded 4-(tert-butyl-dimethyl-silanyloxymethyl)-1-phenyl-1H-pyridin-2-one as a white solid. $^1$H NMR (400 MHz, $CDCl_3$) δ 7.49–7.47 (m, 2H); 7.43–7.39 (m, 3H); 7.29–7.28 (d, 2H); 6.65 (s, 1H); 6.19 (d, 2H); 4.59 (s, 2H); 0.97 (s, 9H); 0.14 (s, 6H).

Step 4: 4-Hydroxymethyl-1-phenyl-1H-pyridin-2-one 4-(Tert-butyl-dimethyl-silyloxymethyl)-1-phenyl-1H-pyridin-2-one from Step 3 (1.3 g) was dissolved in TBAF in 1M THF (15 mL). The clear reaction mixture was stirred for 16 hours. The reaction mixture was concentrated and purified on a column of silica eluting with 10% MeOH/EtOAc to yield 4-hydroxymethyl-1-phenyl-1H-pyridin-2-one as a tan solid. $^1$H NMR (400 MHz, $CDCl_3$) δ 7.5–7.47 (m, 2H); 7.43 (d, 1H); 7.38–7.36 (m, 2H); 7.32–7.30 (d, 1H) 6.67 (s, 1H); 6.23 (d, 1H) 4.57 (d, 2H).

Step 5: 4-Bromomethyl-1-phenyl-1H-pyridin-2-one

4-Hydroxymethyl-1-phenyl-1H-pyridin-2-one from Step 4 (1.0 g, 5 mmol) was dissolved in $CH_2Cl_2$. $CBr_4$ (6 mmol, 2 g) was added and the reaction mixture was cooled to 0°. $PPh_3$ (6 mmol, 2.0 g) was added dropwise in $CH_2Cl_2$. The reaction mixture was stirred at 0° for 15 minutes and then warmed to room temperature. The reaction mixture was concentrated and purified on a column of silica eluting with (30% EtOAc/hexane to 50% EtOAc/hexane) to give 4-bromomethyl-1-phenyl-1H-pyridin-2-one (8, x=H) as a white solid.

$^1$H NMR (400 MHz, $CDCl_3$) δ 7.52–7.48 (m, 2H); 7.45–7.43 (d, 1H); 7.38–7.33 (m, 3H); 6.64 (s, 1H); 6.30–6.28 (d, 1H); 4.25 (d, 2H).

Step 6: 4-(1-Trityl-1H-imidazol-4-ylmethyl)-benzonitrile

To a suspension of activated zinc dust (3.57 g, 54.98 mmol) in THF (50 mL) was added dibromoethane (0.315 mL, 3.60 mmol) and the reaction stirred under argon for 45 minutes, at 20° C. The suspension was cooled to 0° C. and α-bromo-p-tolunitrile (9.33 g, 47.6 mmol) in THF (100 mL) was added dropwise over a period of 10 minutes. The reaction was then allowed to stir at 20° C. for 6 hours and bis(triplhenylphosphine)Nickel II chloride (2.40 g, 3.64 mmol) and 5-iodotrityl imidazole (15.95 g, 36.6 mmol) were added in one portion. The resulting mixture was stirred 16 hours at 20° C. and then quenched by addition of saturated NH4Cl solution (100 mL) and the mixture stirred for 2 hours. Saturated aq. $NaHCO_3$ solution was added to give a pH of 8 and the solution was extracted with EtOAc (2×250 mL), dried ($MgSO_4$) and the solvent evaporated in vacuo. The residue was chromatographed (silica gel, 0–20% EtOAc in CH2Cl2) to afford the title compound as a white solid.

$^1$H NMR ($CDCl_3$, 400 Mz) δ (7.54 (2H, d, J=7.9 Hz), 7.38(1H, s), 7.36–7.29 (11H, m), 7.15–7.09(6H, m), 6.58 (1H, s) and 3.93(2H, s) ppm.

Step 7: 4-[3-(2-Oxo-1-phenyl-1,2-dihydropyridin-4-ylmethyl)-3H-imidazol-4-ylmethyl]benzonitrile, hydrochloride 4-Bromomethyl-1-phenyl-1H-pyridin-2-one from Step 5 (1.1 g, 4.1 mmol) and 4-(1-trityl-1H-imidazol-4-ylmethyl)-benzonitrile from Step 6 (4.1 mmol, 1.7 g) were suspended in $CH_3CN$ and heated to 80°. After 30 minutes the reaction became homogeneous. The reaction mixture was heated to 80° for 16 hours. The heterogeneous reaction mixture was concentrated, taken up in MeOH and refluxed for 1 hour. The reaction mixture was cooled, diluted with $CHCl_3$ and washed with saturated $NaHCO_3$. The aqueous layer was back extracted 4 times with $CHCl_3$. The organic layers were combined, washed with brine, dried ($MgSO_4$), filtered and concentrated to yield a yellow solid which was purified by flash chromatography (7% i-PrOH/CHCl₃ saturated with NH₃). Purest fractions were collected and concentrated to yield a white solid which was triturated with EtOAc. The solids were filtered, washed with EtOAc and dried under hi-vacuum for 16 hours to yield 4-[3-(2-Oxo-1-phenyl-1,2-dihydropyridin-4-ylmethyl)-3H-imidazol-4-ylmethyl] benzonitrile, hydrochloride as a white solid.

$^1$H NMR (400 MHz, CDCl₃) δ 7.61 (s, 1H); 7.58–757 (d, 2H) 7.52–7.49 (m, 2H); 7.46–7.44 (d, 1H); 7.34–7.32 (d, 2H); 7.26–7.25 (m, 2H); 6.97 (s, 1H); 6.20 (s, 1H); 5.77 (d, 1H); 4.77 (d, 2H); 3.96 (s, 2H).

EXAMPLE 2

4-{3-[1-(3-Chloro-phenyl)-2-oxo-1,2-dihydropyridin-4-ylmethyl]-3H-imidazol-4-ylmethyl}benzonitrile was prepared in a manner substantially similar to the procedure described above for 4-[3-(2-oxo-1-phenyl-1,2-dihydropyridin-4-ylmethyl)-3H-imidazol-4-ylmethyl] benzonitrile, hydrochloride, but substituting 3-chloroiodobenzene for the iodobenzene in Step 3.

$^1$H NMR (400 MHz, DMSO d₆) δ 9.25 (s, 1H); 7.73–7.71 (d, 2H); 7.61–7.58 (m, 2H); 7.54–7.52(m, 2H); 7.46 (s, 1H); 7.38–7.36 (d, 2H); 7.30 (m, 1H); 6.07–6.05 (d, 1H); 5.87 (s, 1H); 5.34 (s, 2H); 4.20 (s, 2H).

EXAMPLE 3

4-[3-(2-Oxo-2H-[1,2']bipyridinyl-4-ylmethyl)-3H-imidazol-4-ylmethyl]-benzonitrile hydrochloride salt was prepared in a manner substantially similar to the procedure described above for 4-[3-(2-oxo-1-phenyl-1,2-dihydropyridin-4-ylmethyl)-3H-imidazol-4-ylmethyl] benzonitrile, hydrochloride, but substituting 2-bromopyridine for the iodobenzene in Step 3.

$^1$H NMR (400 MHz, CDCl₃) δ 9.26 (s, 1H); 8.60–8.59 (d, 1H); 8.00–7.96 (t, 1H); 7.81–7.79(d, 1H); 7.71–7.69 (d, 3H); 7.64 (s, 1H); 7.51–7.48 (m, 1H); 7.37–7.35 (d, 2H); 6.11–6.09 (d, 1H); 5.91 (s, 1H); 5.36 (s, 2H); 4.20 (s, 2H).

EXAMPLE 4

4-[3-(6'-Methyl-2-oxo-2H-[1,2']bipyridinyl-4-ylmethyl)-3H-imidazol-4-ylmethyl]-benzonitrile was prepared in a manner substantially similar to the procedure described above for 4-[3-(2-oxo-1-phenyl-1,2-dihydropyridin-4-ylmethyl)-3H-imidazol-4-ylmethyl]benzonitrile, hydrochloride, but substituting 2-bromo-6-methylpyridine for the iodobenzene in Step 3.

$^1$H NMR (400 MHz, CDCl₃) δ 7.81–7.79 (d, 1H); 7.75–7.71 (m, 1H); 7.68–7.61 (d, 1H); 7.58–7.56(m, 3H); 7.1–7.24 (m, 3H); 6.96 (s, 1H); 6.12 (s, 1H); 5.83–5.81(dd, 1H); 4.75 (s, 2H); 3.92 (s, 2H); 2.58 (s, 3H).

EXAMPLE 5

4-{3-[1-(3-Chloro-phenyl)-2-oxo-1,2-dihydro-pyridin-4-ylmethyl]-3H-imidazol-4-ylmethyl}-2-methoxy-benzonitrile was prepared in a manner substantially similar to the procedure described above for 4-{3-[1-(3-Chloro-phenyl)-2-oxo-1,2-dihydropyridin-4-ylmethyl]-3H-imidazol-4-ylmethyl}benzonitrile, but substituting 4-(1-trityl-1H-imidazol-4-ylmethyl)-3-methoxybenzonitrile for 4-(1-trityl-1 H-imidazol-4-ylmethyl)-benzonitrile in Step 7.

$^1$H NMR (400 MHz, CDCl₃) δ 7.58 (br s, 1H); 7.48–7.41 (m, 3H); 7.36 (s, 1H); 7.02(br s, 1H); 6.80–6.78 (d, 1H); 6.69 (s, 1H); 6.14 (s, 1H); 5.77–5.75 (dd, 1H); 4.77 (s, 2H); 3.92 (s, 2H); 3.86 (s, 3H).

EXAMPLE 6

4-[3-(2-Oxo-1-pyrimidin-2-yl-1,2-dihydro-pyridin-4-ylmethyl)-3H-imidazol-4-ylmethyl]-benzonitrile was prepared in a manner substantially similar to the procedure described above for 4-[3-(2-oxo-1-phenyl-1,2-dihydropyridin-4-ylmethyl)-3H-imidazol-4-ylmethyl] benzonitrile, hydrochloride, but substituting 2-chloropyrimidine for the iodobenzene in Step 3.

$^1$H NMR (400 MHz, CDCl₃) δ 8.92 (d, 2H); 7.58–7.55 (m, 3H); 7.50–7.48 (d, 1H); 7.42–7.40(t, 1H); 7.22–7.20 (d, 2H); 6.98 (s, 1H); 6.20 (s, 1H); 5.74–5.71 (dd, 1H); 4.77 (s, 2H); 3.92 (s, 2H).

EXAMPLE 7

4-{3-[1-(6-chloro-pyrazin-2-yl)-2-oxo-1,2-dihydro-pyridin-4-ylmethyl]-3H-imidazol-4ylmethyl}-benzonitrile was prepared in a manner substantially similar to the procedure described above for 4-[3-(2-oxo-1-phenyl-1,2-dihydropyridin-4-ylmethyl)-3H-imidazol-4-ylmethyl] benzonitrile, hydrochloride, but substituting 2,6-dichloropyrazine for the iodobenzene in Step 3.

$^1$H NMR (400 MHz, CDCl₃) δ 9.34 (s, 1H); 8.61 (s, 1H); 7.88–7.86 (d, 1H); 7.58–7.63(m, 3H); 7.24–7.21 (d, 2H); 6.98 (s, 1H); 6.08 (s, 1H); 5.92–5.90 (dd, 1H); 4.76 (s, 2H); 3.92 (s, 2H).

EXAMPLE 8

4-[3-(3'-Methyl-2-oxo-2H-[1,2']bipyridinyl-4-ylmethyl)-3H-imidazol-4-ylmethyl]-benzonitrile was prepared in a manner substantially similar to the procedure described above for 4-[3-(2-oxo-1-phenyl-1,2-dihydropyridin-4-ylmethyl)-3H-imidazol-4-ylmethyl]benzonitrile, hydrochloride, but substituting 2-bromo-3-mehtylpyridine for the iodobenzene in Step 3.

$^1$H NMR (400 MHz, CDCl₃) δ 8.45–8.44 (D, 1H); 7.71–7.69 (d, 1H); 7.60–7.57 (m, 3H); 7.36–7.29(m, 2H); 7.25–7.23 (d, 2H); 6.96 (s, 1H); 6.15 (s, 1H); 5.82–5.80 (dd, 1H); 4.78 (s, 2H); 3.93–3.92 (d, 2H); 2.22 (s, 3H).

EXAMPLE 9

4-[3-(6'-chloro-2-oxo-2H-1,2']bipyridinyl-4-ylmethyl)-3H-imidazol-4-ylmethyll-benzonitrile was prepared in a manner substantially similar to the procedure described above for 4-[3-(2-oxo-1-phenyl-1,2-dihydropyridin-4-ylmethyl)-3H-imidazol-4-ylmethyl]benzonitrile, hydrochloride, but substituting 2,6-dichloropyridine for the iodobenzene in Step 3.

$^1$H NMR (400 MHz, CDCl₃) δ 7.96–7.94 (dd, 1H); 7.88–7.86 (d, 1H); 7.84–7.80 (t, 1H); 7.57–7.55 (m, 3H); 7.38–7.35 (dd, 1H); 7.23–7.21 (d, 2H); 6.97 (s, 1H); 5.88–5.86 (dd, 1H); 4.75 (s, 2H); 3.92 (s, 2H).

EXAMPLE 10

4-[3-(6-'Triflouromethyl-2-oxo-2H-[1,2']bipyridinyl-4-ylmethyl)-3H-imidazol-4-ylmethyl]-benzonitrile was prepared in a manner substantially similar to the procedure described above for 4-[3-(2-oxo-1-phenyl-1,2-dihydropyridin-4-ylmethyl)-3H-imidazol-4-ylmethyl] benzonitrile, hydrochloride, but substituting 2-chloro-6-trifluoromethylpyridine for the iodobenzene in Step 3.

$^1$H NMR (400 MHz, CDCl₃) δ 8.27–8.25 (d, 1H); 8.06–8.02 (t, 1H); 7.97–7.95 (d, 1H); 7.72–7.70(d, 1H); 7.57–7.55 (m, 3H); 7.26–7.22 (m, 2H); 6.98 (s, 1H); 6.05 (s, 1H); 5.93–5.90 (dd, 1H); 4.77 (s, 2H); 3.93 (s, 2H).

EXAMPLE 11

4-{3-[1-(6-Chloro-pyrimidin-2-yl)-2-oxo-1,2-dihydro-pyridin-4-ylmethyl]-3H-imidazol-4ylmethyl}-benzonitrile was prepared in a manner substantially similar to the procedure described above for 4-[3-(2-oxo-1-phenyl-1,2-dihydropyridin-4-ylmethyl)-3H-imidazol-4-ylmethyl] benzonitrile, hydrochloride, but substituting 2,4-dichloropyrimidine for the iodobenzene in Step 3.

¹H NMR (400 MHz, CDCl₃) δ 8.74–8.72 (d, 1H); 8.31–8.30 (d, 1H); 8.18–8.17 (d, 1H); 7.57–7.55(m, 3H); 7.23–7.21 (d, 2H); 6.99 (s, 1H); 5.99 (s, 1H); 5.94–5.92 (dd, 1H); 4.76 (s, 2H); 3.92 (s, 2H).

EXAMPLE 12

4-{3-[1-(6-Chloro-pyrazin-2-yl)-2-oxo-1,2-dihydro-pyridin-4-ylmethyl]-3H-imidazol-4ylmethyl}-2-methoxy-benzonitrile was prepared in a manner substantially similar to the procedure described above for 4-[3-(2-oxo-1-phenyl-1,2-dihydropyridin-4-ylmethyl)-3H-imidazol-4-ylmethyl]benzonitrile, hydrochloride, but substituting 2,6-dichloropyrazine for the iodobenzene in Step 3.

¹H NMR (400 MHz, CDCl₃) δ 9.34 (s, 1H); 8.62 (s, 1H); 7.88–7.86 (d, 1H); 7.58(s, 1H); 7.47–7.44 (d, 1H); 7.01 (1, 1H); 6.78–6.75 (d, 1H); 6.68 (s, 1H); 6.08 (s, 1H); 5.93–5.90 (d, 1H); 4.78 (s, 2H); 3.91 (s, 2H); 3.86 (s, 3H).

EXAMPLE 13

4-{3-[1-(6-Chloro-4-methyl-pyrimidin-2-yl)-2-oxo-1,2-dihydro-pyridin-4-ylmethyl]-3H-imidazol-4ylmethyl}-benzonitrile was prepared in a manner substantially similar to the procedure described above for 4-[3-(2-oxo-1-phenyl-1,2-dihydropyridin-4-ylmethyl)-3H-imidazol-4-ylmethyl]benzonitrile, hydrochloride, but substituting 2,4-dichloro-6-methylprimidine for the iodobenzene in Step 3.

¹H NMR (400 MHz, CDCl₃) δ 8.12–8.10 (m, 2H); 7.56–7.54 (d, 3H); 7.22–7.20 (d, 2H); 6.99-(s, 1H); 5.97 (s, 1H); 5.92–5.89 (dd, 1H); 4.75 (s, 2H); 3.92 (s, 2H); 2.63 (d, 3H).

EXAMPLE 14

3-[3-(6'-chloro-2-oxo-2H-[1,2']bipyridinyl-4-ylmethyl)-3H-imidazol-4-ylmethyl]-benzonitrile was prepared in a manner substantially similar to the procedure described above for 4-[3-(6'-chloro-2-oxo-2H-[1,2'] bipyridinyl-4-ylmethyl)-3H-imidazol-4-ylmethyl]-benzonitrile, but substituting 3-(1-trityl-1H-imidazol-4-ylmethyl)-benzonitrile for 4-(1-trityl-1H-imidazol-4-ylmethyl)-benzonitrile in Step 7.

¹H NMR (400 MHz, CDCl₃) δ 7.96–7.80 (m, 3H); 7.63–7.51 (m, 2H); 7.42–7.29 (m, 4H); 6.95(s, 1H); 6.34 (s, 1H); 5.89–5.87 (d, 1H); 4.78 (s, 2H); 3.90 (s, 2H).

EXAMPLE 15

4-[3-(5'-Cyano-2-oxo-2H-[1,3']bipyridinyl-4-ylmethyl)-3H-imidazol-4-ylmethyl]-benzonitrile was prepared in a manner substantially similar to the procedure described above for 4-[3-(2-oxo-1-phenyl-1,2-dihydropyridin-4-ylmethyl)-3H-imidazol-4-ylmethyl]benzonitrile, hydrochloride, but substituting 3-cyano-5-bromopyridine for the iodobenzene in Step 3.

¹H NMR (400 MHz, CDCl₃) δ 8.00–7.81 (m, 2H); 7.56–7.54 (m, 3H); 7.41 (m, 2H), 7.22–7.20 (d, 2H, J=7.9 Hz); 6.99-(s, 1H); 5.96 (s, 1H); 5.91–5.88 (dd, 1H); 4.75 (s, 2H); 3.89 (s, 2H).

EXAMPLE 16

4-[3-(4'-Trifluoromethyl-2-oxo-2H-[1,2']bipyridinyl-4-ylmethyl)-3H-imidazol-4-ylmethyl]-benzonitrile was prepared in a manner substantially similar to the procedure described above for 4-[3-(2-oxo-1-phenyl-1,2-dihydropyridin-4-ylmethyl)-3H-imidazol-4-ylmethyl]benzonitrile, hydrochloride, but substituting 2-bromo-4-trifluoromethylpyridine for the iodobenzene in Step 3.

¹H NMR (400 MHz, CDCl₃) δ 8.10–7.72 (m, 2H); 7.57–7.55 (m, 3H); 7.44 (m, 2H), 7.22–7.20 (d, 2H,J=7.9 Hz); 6.98 (s, 1H); 5.96 (s, 1H:); 5.91–5.88 (dd, 1H); 4.74 (s, 2H); 3.88 (s, 2H).

EXAMPLE 17

4-[3-(6'-Methoxy-2-oxo-2H-[1,2']bipyridinyl-4-ylmethyl)-3H-imidazol-4-ylmethyl]-benzonitrile was prepared in a manner substantially similar to the procedure described above for 4-[3-(2-oxo-1-phenyl-1,2-dihydropyridin-4-ylmethyl)-3H-imidazol-4-ylmethyl]benzonitrile, hydrochloride, but substituting 2-bromo-6-methoxypyridine for the iodobenzene in Step 3.

¹H NMR (400 MHz, CDCl₃) δ 8.11–7.72 (m, 2H); 7.57–7.55 (m, 3H); 7.46 (m, 2H), 7.23–7.19 (d, 2H, J=7.9 Hz); 6.98 (s, 1H); 5.96 (s, 1H); 5.90–5.85 (dd, 1H); 4.75 (s, 2H); 3.84 (s, 2H); 3.76 (s, 3H).

EXAMPLE 18

4-[3-(3'-Nitro-2-oxo-2H-[1,2']bipyridinyl-4-ylmethyl)-3H-imidazol-4-ylmethyl]-benzonitrile was prepared in a manner substantially similar to the procedure described above for 4-[3-(2-oxo-1-phenyl-1,2-dihydropyridin-4-ylmethyl)-3H-imidazol-4-ylmethyl]benzonitrile, hydrochloride, but substituting 2-bromo-3-nitropyridine for the iodobenzene in Step 3.

¹H NMR (400 MHz, CDCl₃) δ 8.09–7.71 (m, 2H); 7.57–7.55 (m, 3H); 7.52–7.36 (m, 2H), 7.23–7.19 (d, 2H, J=7.9 Hz); 6.98 (s, 1H); 5.95 (s, 1H); 5.90–5.84 (dd, 1H); 4.74 (s, 2H); 3.86 (s, 2H).

EXAMPLE 19

4-[3-(3'-Trifluoromethyl-2-oxo-2H-[1,2']bipyridinyl-4-ylmethyl)-3H-imidazol-4-ylmethyl]-benzonitrile was prepared in a manner substantially similar to the procedure described above for 4-[3-(2-oxo-1-phenyl-1,2-dihydropyridin-4-ylmethyl)-3H-imidazol-4-ylmethyl]benzonitrile, hydrochloride, but substituting 2-chloro-3-trifluoropyridine for the iodobenzene in Step 3.

¹H NMR (400 MHz, CDCl₃) δ 8.11–7.73 (m, 2H); 7.58–7.55 (m, 3H); 7.51–7.39 (m, 2H), 7.24–7.18 (d, 2H, J=7.9 Hz); 6.96 (s, 1H); 5.95 (s, 1H); 5.92–5.82 (dd, 1H); 4.73 (s, 2H); 3.84 (s, 2H).

EXAMPLE 20

4-{3-[1-(6-Trifluromethyl-pyrimidin-2-yl)-2-oxo-1,2-dihydro-pyridin-4-yl methyl]-3H-imidazol-4-ylmethyl}-benzonitrile was prepared in a manner substantially similar to the procedure described above for 4-[3-(2-oxo-1-phenyl-1,2-dihydropyridin-4-ylmethyl)-3H-imidazol-4-ylmethyl]benzonitrile, hydrochloride, but substituting 2-chloro-4-trifluoropyrimidine for the iodobenzene in Step 3.

¹H NMR (400 MHz, CDCl₃) δ 8.13–7.72 (m, 2H); 7.57–7.49 (m, 2H); 7.48–7.39 (m, 2H), 7.26–7.20 (d, 2H, J=7.9 Hz); 6.95 (s, 1H); 5.96 (s, 1H); 5.94–5.83 (dd, 1H); 4.73 (s, 2H); 3.82 (s, 2H).

EXAMPLE 21

4-[5-(4-Bromophenoxy)imidazol-1-ylmethyl]-1-(6-cyanopyrazin-2-yl)-1H-pyridin-2-one Step 1: 4-(4-Bromophenyloxy)imidazole To a mixture of liquid 4-bromophenol (25 g, mp 64–68° C.) at 100–110° C. and its sodium salt [Prepared from 3.5 g (20 mmol) 4-bromo-phenol and sodium metal (0.46 g, 20 mmol) in anhydrous methanol. The resultant solution was concentrated and the residual solvent removed under vacuum overnight], neat methyl N-(cyano-methyl) methanimidate (2 mL, 20 mmol; Hosmane, R. S. et al, *J. Org. Chem.*, p. 1212, 1984) was added dropwise over a period of 10 minutes under a slow stream of dry argon. The resultant mixture was stirred at 100° C. for 2 h, and the reaction product partitioned between methylene chloride (250 mL) and aqueous sodium hydroxide (1 M, 250 mL). The aqueous layer was separated and extracted with methylene chloride (3×50 mL). The organic extracts were combined, washed with brine (50 mL), dried over anhydrous potassium carbonate, filtered and concentrated. The residue was subjected to column chromatography on silica gel eluting with a mixture of 7:3 v/v chloroform and acetone. Collection and concentration of appropriate fractions provided the titled compound as white powder.

$^1$H NMR δ DMSO-$d_6$ 7.49 (1H, s), 7.48 (2H, d, J=9.0 Hz), 6.93 (2H, d, J=9.0 Hz), 6.85 (1H, s).

Step 2: 4-(4-Bromophenyloxy)-1-trityl-1H-imidazole

To a cold (0° C.) solution of 4-(4-bromophenyloxy) imidazole (1.2 g, 5.0 mmol) and triethylamine (0.76 mL, 5.5 mmol) in DMF (5 mL) under an atmosphere of argon, solid trityl chloride (1.46 g, 5.3 mmol) was added. The resultant mixture was stirred at room temp overnight. The product mixture was concentrated onto silica gel, loaded onto a column of silica gel, and eluted with a mixture of 9:1 chloroform and acetone. Collection and concentration of appropriate fractions provided the titled compound as white powder.

Step 3: 4-[5-(4-Bromophenoxy)imidazol-1-ylmethyl]-1-(6-chloro-pyrazin-2-yl)-1H-pyridin-2-one A mixture of 4-(4-bromophenyloxy)-1-trityl-1H-imidazole (0.164 g, 0.34 mmol) and 4-bromomethyl-1-(6-chloro-pyrazin-2-yl)-1H-pyridin-2-one from example 7 (98.5 mg, 0.34 mmol) in anhydrous acetonitrile (10 mL) was heated under reflux at 60° C. for 24 h. The resultant solution was concentrated, and the residue dissolved in a mixture of methanol (10 mL) and 1,2-dichloroethane (1 mL). The solution was heated under reflux for 2 h, and concentrated under vacuum. The residue was subjected to column chromatography on silica gel eluting with 1:1 v/v 6% methanol in chloroform and chloroform saturated with ammonia gas. Collection and concentration of appropriate fractions provided the titled compound.

$^1$H NMR CDCl$_3$ δ 9.33 (1H, s), 8.60 (1H, s), 7.87 (1H, d, J=7.6 Hz), 7.41 (1H, d, J=8.8 Hz), 7.40 (1H, s), 6.92 (1H, d, J=8.8 Hz), 6.67 (1H, s), 6.31 (1H, br s), 6.09 (1H, dd, J=7.6, 1.9 Hz), 4.85 (2H, s).

Step 4: 4-[5-(4-Bromophenoxy)imidazol-1-ylmethyl]-1-(6-cyano-pyrazin-2-yl)-1H-pyridin-2-one A mixture of 4-[5-(4-Bromophenoxy)imidazol-1-ylmethyl]-1-(6-chloropyrazin-2-yl)-1H-pyridin-2-one (79 mg, 0.17 mmol) and zinc cyanide (12 mg, 0.1 mmol) in DMF (1 mL) was purged with argon for 5 min. A solution of tetrakis(triphenylphosphine)palladium(0) (20 mg, 17 μmol) in DMF (0.5 mL) was added. The resultant mixture was stirred under argon at 80° C. overnight, and concentrated under vacuum. The residue was subjected to column chromatography on silica gel eluting with 1:1 v/v 5% methanol in chloroform and chloroform saturated with ammonia gas. Collection, concentration of appropriate fractions, and trituration of the residue with anhydrous ether provided the titled compound as white solid.

$^1$H NMR CDCl$_3$ δ 9.64 (1H, s), 8.89 (1H, s), 7.88 (1H, d, J=7.6 Hz), 7.41 (1H, d, J=9.1 Hz), 7.40 (1H, s), 6.92 (1H, d, J=9.1 Hz), 6.69 (1H, s), 6.32 (1H, br s), 6.13 (1H, dd, J=7.6, 2.0 Hz), 4.86 (2H, s). FAB MS M+1=449/451 1:1.

EXAMPLE 22

4-{5-[1-(3-Chloro-phenyl)-2-oxo-1,2-dihydro-pyridin-4-ylmethtyl]-imidazol-1-ylmethyl}-2-methoxy-benzonitrile Step 1: 4-(tert-butyl-dimethyl-silanyloxymethyl)-1-(3-chlorophenyl)-1H-pyridin-2-one 4-(Tert-butyldimethylsilyloxymethyl)-1H-pyridin-2-one (3.5 g, 14.6 mmol) (prepared as described in Japan Patent 6-80635 22-March(1994) was dissolved in 3-chloroiodobenzene (25 g, 105 mmol) and treated with copper (933 mg, 14.6 mmol) and K$_2$CO$_3$ (2.02 g, 14.6 mmol). The brown slurry was heated to 200° C. for 7 hrs. The reaction mixture was triturated with EtOAc (75 ml) and filtered. The filtrate was concentrated in vacuo and the residue chromatographed (silica gel, EtOAc: hexane 30:70) to afford the title compound.

$^1$H NMR (400 MHz, CDCl$_3$) δ 7.45–7.38(m, 3H), 7.30(m, 1H), 7.26 (d, J=5.3Hz, 1H), 6.65 (s, 1H), 6.19 (d, J=7.1 Hz, 1H), 4.59 (s, 2H), 0.97 (s, 9H), 0.14 (s, 6H) ppm.

Step 2: 4-Hydroxymethyl-1-(3-chlorophenyl)-1H-pyridin-2-one

To a solution of 4-(tert-butyl-dimethyl-silanyloxymethyl)-1-(3-chlorophenyl)-1H-pyridin-2-one (5.11 g, 14.6 mmol) in acetonitrile (75 ml) in a teflon beaker was added hydrogen fluoride-pyridine (2.5 ml, 87.5 mmol) and stirred for 3 hours. The reaction mixture was neutralized with solid and aqueous sodium dicarbonate and then the solvent evaporated in vacuo. The resulting solid residue was extracted with EtOAc, dried (MgSO$_4$), filtered and the solvent was evaporated in vacuo. This residue was chromatographed (silica gel, 80–100% EtOAc:hexane gradient elution) to afford the title compound.

$^1$H NMR (400 MHz, CDCl$_3$) δ 7.45–7.38 (m, 3H), 7.30–7.25 (m, 2H), 6.66 (s, 1H); 6.24 (d, J=7.1 Hz, 1H), 4.58 (d, J=6.0 Hz, 2H), 2.43 (t, J=6.0 Hz, 1H) ppm.

Step 3: 1-(3-chloro-phenyl)-2-oxo-1,2-dihydro-pyridine-4-carbaldehyde

To a solution of 4-hydroxymethyl-1-(3-chlorophenyl)-1H-pyridin-2-one (2.39 g, 10.14 mmol) in CH$_2$Cl$_2$ (250 ml) was added MnO$_2$ (4.41 g, 50.71 mmol) and stirred for 18 hours. The suspension was filtered through celite and the pad washed with additional CH$_2$Cl$_2$ (200 ml). The combined filtrates were evaporated in vacuo and chromatographed (silica gel, 5–20% EtOAc: CH$_2$Cl$_2$ gradient elution) to afford the title compound.

$^1$H NMR (400 MHz, CDCl$_3$) δ 9.93 (s, 1H), 7.47–7.41 (m, 4H), 7.30 (m, 1H), 7.10 (d, J=1.6 Hz, 1H), 6.67 (dd, J=7.1 and 1.6 Hz, 1H) ppm.

Step 4: 1-(3-chloro-phenyl)-4-[hydroxy-(1-trityl-1H-imidazoi-4-yl)-methyl]-1H-pyridin-2-one To a solution of trityl-4-iodoimidazole (3.51 g, 8.04 mmol) in CH$_2$Cl$_2$ (50 ml) at room temperature was added a solution of ethyl-magnesium bromide (2.81 ml of a 3M solution in diethylether, 8.43 mmol) and the mixture stirred for 2 hr. The aldehyde from step 3 (1.79 g, 7.66 mmol) in CH$_2$Cl$_2$ (50 ml) was added and the reaction was stirred a further 18 hrs at room temperature. Saturated NH$_4$Cl solution (200 ml) was added and the reaction stirred until the solids had dissolved. This mixture was extracted with CH$_2$Cl$_2$ (2×250 ml). The combined extracts were washed with brine, dried (MgSO$_4$) and evaporated in vacuo. The residue was chromatographed (silica gel, 5:95 MeOH: CH$_2$Cl$_2$) to afford the title compound. $^1$H NMR (400 MHz, CDCl$_3$) δ 7.44(2, 1H), 7.42–7.31(m, 10H), 7.30–7.21(m, 4H), 7.15–7.09(m, 6H), 6.78(s, 1H), 6.67(s, 1H), 6.37(dd, J=7.1 and 1.8 Hz, 1H), 5.56(d, J=5.2 Hz, 1H), and 4.60(d, J=5.2 Hz, 1H) ppm.

Step 5: Thiocarbonic acid O-[[1-(3-chloro-phenyl)-2-oxo-1,2-dihydro-pyridin-4-yl]-(1-trityl-1H-imidazol-4-yl)-methyl] ester O-phenyl ester To a solution of the alcohol from Step 4 (2.67 g, 5.02 mmol) in CH$_2$Cl$_2$ (50 ml) at 0° C. was added DMAP (1.34, 11.0 mmol) and phenylthiochloroformate (694 μl, 5.522 mmol) and the mixture was stirred at room temperature for 18 hrs. The pH of the solution was adjusted to 8.5 with sat NaHCO$_3$ solution and the aqueous extracted with CH$_2$Cl$_2$ (2×200 ml). The combined extracts were washed with brine, dried (MgSO$_4$) and evaporated in vacuo. The residue was chromatographed (silica gel, MeOH: CH$_2$Cl$_2$ 2:98 to 3:97 gradient elution) to afford the title compound.

$^1$H NMR (400 MHz, CDCl$_3$) δ 7.45(s, 1H), 7.44–7.30(m, 13H), 7.30–7.19(m, 5H), 7.17–7.08(m, 7H), 6.84(s, 1H), 6.75(s, 1H), 6.50(d, J=8 Hz, 1H) and 5.55(s, 1H) ppm.

Step 6: 1-(3-Chloro-phenyl)-4-(1-trityl-1H-imidazol-4-ylmethyl)-1H-pyridin-2-one To a solution of the thiocarbonate from Step 5 (0.95, 1.4 mmol) in benzene (40 ml) at room temperature was added tributyl tin hydride (1.13 ml, 4.19 mmol) and AIBN (46 mg, 0.28 mmol). The mixture was degassed by bubbling argon through for 15 min and the mixture was heated at 85° C. for 18 hrs while distilling off most of solvent. The residue was chromatographed (silica gel, MeOH: CH$_2$Cl$_2$ 2:98 to 4:96 gradient elution) to afford the title compound.

$^1$H NMR (400 MHz, CDCl$_3$) δ 7.43–7.22(m, 16H), 7.19–7.07(m, 9H), 6.68(s, 1H), 6.45(s, 1H), 6.21(d, J=7.0 Hz, 1H) and 3.74(2, 2H) ppm.

Step 7: 4-{5-[1-(3-Chloro-phenyl)-2-oxo-1,2-dihydro-pyridin-4-ylmethyl]-imidazol-1-ylmethyl}-2-methoxy-benzonitrile To a solution of 1-(3-Chloro-phenyl)-4-(1-trityl-1H-imidazol-4-ylmethyl)-1H-pyridin-2-one (272 mg, 0.527 mmol) from step 6 and 4-hydroxymethyl-2-methoxy-benzonitrile (90.3 mg, 0.55 mmol) in CH$_2$Cl$_2$ cooled to −78° C. over dry ice/acetone bath was added N,N-diisopropylethylamine (192 µl, 1.1 mmol) and trifluoromethane-sulfonic anhydride(93 µl, 0.55 mmol). The reaction was allowed to slowly warm to room temperature and stirred overnight. The reaction was diluted with methanol (10 mL), heated to reflux for 2 h, cooled and the solvent evaporated in vacuo. The residue was partitioned between sat. Na$_2$CO$_3$ (20 ml) and CH$_2$Cl$_2$(2×50 ml). The organic extracts were dried (MgSO$_4$) and evaporated in vacuo. The residue was chromatographed (silica gel, MeOH: CH$_2$Cl$_2$ 3:97 to 4:96 to 10:90 gradient elution) to afford the free base which was converted to the hydrochloride salt to afford the title compound as an off white solid.

$^1$H NMR (400 MHz, CD$_3$OD) δ 9.19(s, 1H), 7.68(s, 1H), 7.56(d, J=8 Hz, 1H), 7.54–7.49(m, 2H), 7.47–7.38(m, 2H), 7.28(dt, J=7.0 and 2 Hz, 1H), 7.01(s, 1H), 6.83(d, J=8 Hz, 1H), 6.18(dd, J=7 and 2 Hz, 1H), 6.05(s, 1H), 5.57(2, 2H), 4.07(s, 2H) and 3.91(s, 3H) ppm. Elemental Analysis cald C$_{24}$H$_{19}$ClN$_4$O$_2$ HCl 0.2 C$_4$H$_8$O 0.95 H$_2$O: C, 59.33; H, 4.72; N, 11.16. Found: C, 59.06; H, 7.06; N, 10.85. HRMS (M$^+$) cald: 431.1269; Found: 431.1271.

EXAMPLE 23

In vitro inhibition of ras farnesyl transferase

*Assays of farnesyl-protein transferase.* Partially purified bovine FPTase and Ras peptides (Ras-CVLS, Ras-CVIM and Ras-CAIL) were prepared as described by Schaber et al., *J. Biol. Chem.* 265:14701–14704 (1990), Pompliano, et al., *Biochemistry* 31:3800 (1992) and Gibbs et al., *PNAS* U.S.A. 86:6630–6634 (1989), respectively. Bovine FPTase was assayed in a volume of 100 µl containing 100 mM N-(2-hydroxy ethyl) piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 µg/ml FPTase at 31° C. for 60 min. Reactions were initiated with FPTase and stopped with 1 ml of 1.0 M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 µM ZnCl$_2$ and 100 nM Ras-CVIM were added to the reaction mixture. Reactions were performed for 30 min., stopped with 100 µl of 30% (v/v) trichloroacetic acid (TCA) in ethanol and processed as described above for the bovine enzyme.

The compounds of the instant invention described in the above Examples 1–22 were tested for inhibitory activity against human FPTase by the assay described above and were found to have IC$_{50}$ of <50 µM.

EXAMPLE 24

In vivo ras farnesylation assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemented with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13–259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

EXAMPLE 25

In vivo growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10$^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound of the formula B-1:

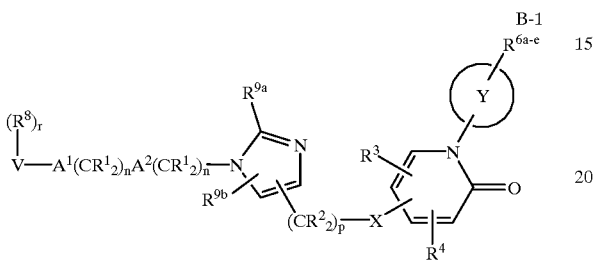

wherein:

Y is selected from: 5, 6 or 7 member carbocyclic ring;

$R^1$ is selected from: hydrogen, $C_3$–$C_{10}$ cycloalkyl, $R^{10}O$—, —$N(R^{10})_2$, F or $C_1$–$C_6$ alkyl;

$R^2$ is independently selected from:
  a) hydrogen,
  b) aryl, $C_3$–$C_{10}$ cycloalkyl, $R^{10}O$—, —$N(R^{10})_2$, F or $C_2$–$C_6$ alkenyl,
  c) unsubstituted or substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $R^{10}O$— and —$N(R^{10})_2$;

$R^3$ and $R^4$ are independently selected from:
  a) hydrogen,
  b) unsubstituted or substituted aryl, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

$R^{6a}$, $R^{6b}$, $R^{6c}$, $R^{6d}$ and $R^{6e}$ are independently selected from:
  a) hydrogen,
  b) unsubstituted or substituted aryl, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $(R^{10})_2NS(O)_2$—, $R^{11}S(O)_mNR^{10}$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $C_2$–$C_6$ alkynyl, $R^{12}O$—, $R^{11}$ $S(O)_m$—, $R^{10}C(O)NR^{10}$—, $(R^{10})_2NC(O)$—, $(R^{10})_2$ $NS(O)_2$—, $R^{11}S(O)_mNR^{10}$—, $R^{10}{}_2N$—$C(NR^{10})$—, CN, $R^{10}C(O)$—, $N_3$, —$N(R^{10})_2$, and $R^{11}OC(O)$—$NR^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—$CH_2$—, —$(CH_2)_4$— and —$(CH_2)_3$—;

$R^8$ is independently selected from:
  a) hydrogen,
  b) aryl, substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, $(R^{10})_2NC(O)$—, $(R^{10})_2NS(O)_2$—, $R^{11}S(O)_mNR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $(R^{10})_2NS(O)_2$—, $R^{11}S(O)_mNR^{10}$—, $R^{10}C(O)$—, —$N(R^{10})_2$, or $R^{11}OC(O)NR^{10}$—;

$R^{9a}$ and $R^{9b}$ are independently hydrogen, $C_1$–$C_6$ alkyl, trifluoromethyl and halogen;

$R^{10}$ is independently selected from hydrogen, $C_1$–$C_6$ alkyl, amino-$C_1$–$C_6$ alkyl, N-(unsubstituted or substituted benzolyl)-amino-$C_1$–$C_6$ alkyl, ($C_1$–$C_6$ alkyl)$_2$-amino-$C_1$–$C_6$ alkyl, acetylamino-$C_1$–$C_6$ alkyl, phenyl-$C_1$–$C_6$ alkyl, 2,2,2-trifluoroethyl, aryl and substituted aryl;

$R^{11}$ is independently selected from $C_1$–$C_6$ alkyl and aryl;

$R^{12}$ is independently selected from hydrogen, $C_1$–$C_6$ alkyl, $C_1$–C6 aralkyl, $C_1$–$C_6$ substituted aralkyl, aryl, substituted aryl, $C_1$–$C_6$ perfluoroalkyl, 2-aminoethyl and 2,2,2-trifluoroethyl;

$A^1$ and $A^2$ are independently selected from: a bond, —CH=CH—, —C≡C—, —C(O)—, —C(O)NR$^{10}$—, O, —N(R$^{10}$)—, or S(O)$_m$;

V is aryl;

X is a bond, —CH=CH—, —C(O)NR$^{10}$—, —NR$^{10}$C(O)—, —NR$^{10}$—, O or —C(=O)—;

m is 0, 1 or 2;

n is independently 0, 1, 2, 3 or 4;

p is 0, 1, 2, 3 or 4; and r is 0 to 5;

or a pharmaceutically acceptable salt thereof.

2. A compound of the formula C-1:

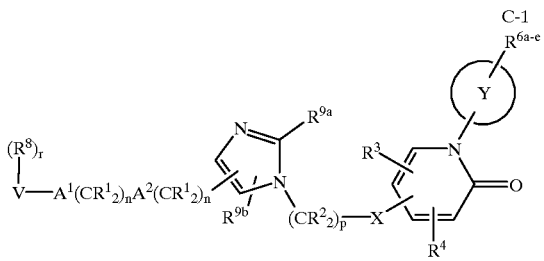

wherein:

Y is selected from: 5, 6 or 7 member carbocyclic ring;

$R^1$ is selected from: hydrogen, $C_3$–$C_{10}$ cycloalkyl, $R^{10}O$—, —$N(R^{10})_2$, F or $C_1$–$C_6$ alkyl;

$R^2$ is independently selected from:
  a) hydrogen,
  b) aryl, $C_3$–$C_{10}$ cycloalkyl, $R^{10}O$—, —$N(R^{10})_2$, F or $C_2$–$C_6$ alkenyl, c) unsubstituted or substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $R^{10}O$— and —$N(R^{10})_2$;

$R^3$ and $R^4$ are independently selected from:
a) hydrogen,
b) unsubstituted or substituted aryl, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $CN(R^{10})_2NC(O)$—, $R^{10}{}_2N$—$C(NR^{10})$—, $CN$, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, $CN$, $R^{10}C(O)$—, $N_3$, —$N(R^{10})_2$, and $R^{11}OC(O)$—$NR^{10}$—;

$R^{6a}$, $R^{6b}$, $R^{6c}$, $R^{6d}$ and $R^{6e}$ are independently selected from:
a) hydrogen,
b) unsubstituted or substituted aryl, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{11}S(O)_2NR^{10}$—, $(R^{10})_2NS(O)_2$—, $R^{10}{}_2N$—$C(NR^{10})$—, $CN$, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{11}S(O)_2 NR^{10}$—, $(R^{10})_2NS(O)_2$—, $R^{10}{}_2N$—$C(NR^{10})$—, $CN$, $R^{10}C(O)$—, $N_3$, —$N(R^{10})_2$, and $R^{11}OC(O)$—$NR^{10}$—; or any two of $R^{6a}$, $R^{6b}$, $R^{6c}$, $R^{6d}$ and $R^{6e}$ on adjacent carbon atoms are combined to form a diradical selected from —CH═CH—CH═CH—, —CH═CH—CH$_2$—, —(CH$_2$)$_4$— and —(CH$_2$)$_3$—;

$R^8$ is independently selected from:
a) hydrogen,
b) aryl, substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, $(R^{10})_2NC(O)$—, $R^{11}S(O)_2NR^{10}$—, $(R^{10})_2NS(O)_2$—, $CN$, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2NC(O)$—, $R^{11}S(O_2NR^{10}$—, $(R^{10})_2NS(O)_2$—, $(R^{10})_2N$—$C(NR^{10})$—, $R^{10}C(O)$—, —$N(R^{10})_2$, or $R^{11}OC(O)NR^{10}$—;

$R^{9a}$ and $R^{9b}$ are independently hydrogen, $C_1$–$C_6$ alkyl, trifluoromethyl and halogen;

$R^{10}$ is independently selected from hydrogen, $C_1$–$C_6$ alkyl, amino-$C_1$–$C_6$ alkyl, N-(unsubstituted or substituted benzolyl)-amino-$C_1$–$C_6$ alkyl, ($C_1$–$C_6$ alkyl)$_2$-amino-$C_1$–$C_6$ alkyl, acetylamino-$C_1$–$C_6$ alkyl, phenyl-$C_1$–$C_6$ alkyl, 2,2,2-trifluoroethyl, aryl and substituted aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, aryl, substituted aryl, $C_1$–$C_6$ perfluoroalkyl, 2-aminoethyl and 2,2,2-trifluoroethyl;

$A^1$ and $A^2$ are independently selected from: a bond, —CH═CH—, —C≡C—, —C(O)—, —C(O)NR$^{10}$—, O, —N(R$^{10}$)—, or S(O)$_m$;

V is aryl;

X is a bond, —CH═CH—, —C(O)NR$^{10}$—, —NR$^{10}$C(O)—, —NR$^{10}$—, O or —C(═O)—;

m is 0, 1 or 2;

n is independently 0, 1, 2, 3 or 4;

p is 0, 1, 2, 3 or 4, provided that p is not 0 if X is a bond or O; and r is 0 to 5;

or a pharmaceutically acceptable salt thereof.

3. The compound according to claim 1 of the formula D-1:

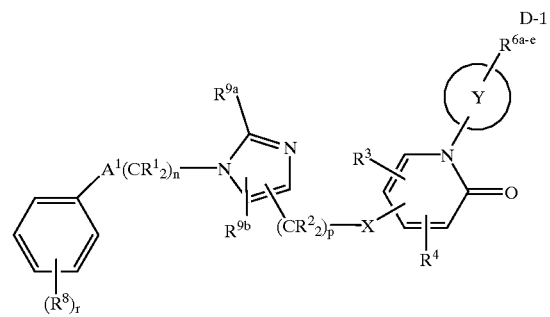

wherein:

Y is selected from: 5, 6 or 7 member carbocyclic ring;

$R^1$ is selected from: hydrogen, $C_3$–$C_{10}$ cycloalkyl or $C_1$–$C_6$ alkyl;

$R^2$ is independently selected from:
a) hydrogen,
b) aryl, $C_3$–$C_{10}$ cycloalkyl, $R^{10}O$—, —$N(R^{10})_2$, F or $C_2$–$C_6$ alkenyl,
c) $C_1$–$C_6$ alkyl unsubstituted or substituted by aryl, $C_3$–$C_{10}$ cycloalkyl, $C_2$–$C_6$ alkenyl, $R^{10}O$—, or —$N(R^{10})_2$;

$R^3$ is selected from:
a) hydrogen,
b) unsubstituted or substituted aryl, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, $CN$, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, $CN$, $R^{10}C(O)$—, $N_3$, —$N(R^{10})_2$, and $R^{11}OC(O)$—$NR^{10}$—;

$R^4$ is selected from H, halogen, $C_1$–$C_6$ alkyl and $CF_3$;

$R^{6a}$, $R^{6b}$, $R^{6c}$, $R^{6d}$ and $R^{6e}$ are independently selected from:
a) hydrogen,
b) unsubstituted or substituted aryl, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, $CN$, $NO_2$, $R^{10}C(O)$—, $N_3$, —$N(R^{10})_2$, or $R^{11}OC(O)NR^{10}$—, c) unsubstituted $C_1$–$C_6$ alkyl, d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—$CH_2$—, —$(CH_2)_4$— and —$(CH_2)_3$—;

$R^8$ is independently selected from:
  a) hydrogen,
  b) aryl, substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, $(R^{10})_2NC(O)$—, CN, $NO_2$, $(R^{10})_2N$—$C(NR^{10})$—, $R^{10}C(O)$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2NC(O)$—, $(R^{10})_2N$—$C(NR^{10})$—, $R^{10}C(O)$—, —$N(R^{10})_2$, or $R^{11}OC(O)NR^{10}$—;

$R^{9a}$ and $R^{9b}$ are independently hydrogen, ethyl, cyclopropyl or methyl;

$R^{10}$ is independently selected from hydrogen, $C_1$–$C_6$ alkyl, amino-$C_1$–$C_6$ alkyl, N-(unsubstituted or substituted benzolyl)-amino-$C_1$–$C_6$ alkyl, $(C_1$–$C_6$ alkyl)$_2$-amino-$C_1$–$C_6$ alkyl, acetylamino-$C_1$–$C_6$ alkyl, phenyl-$C_1$–$C_6$ alkyl, 2,2,2-trifluoroethyl, aryl and substituted aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, substituted aryl, $C_1$–$C_6$ perfluoroalkyl, 2-aminoethyl and 2,2,2-trifluoroethyl;

$A^1$ is selected from: a bond, —C(O)—, O, —$N(R^{10})$—, or $S(O)_m$;

X is a bond, —CH=CH—, —C(O)$NR^{10}$—, —$NR^{10}C(O)$—, —$NR^{10}$—, O or —C(=O)—, n is 0 or 1; provided that n is not 0 if $A^1$ is a bond, O, —$N(R^{10})$— or $S(O)_m$;

m is 0, 1 or 2;

p is 0, 1, 2, 3 or 4; and r is 0, 1 or 2;

or a pharmaceutically acceptable salt thereof.

4. The compound according to claim 2 of the formula E-1:

E-1 wherein:

Y is selected from: 5, 6 or 7 member carbocyclic ring;

$R^1$ is selected from: hydrogen, $C_3$–$C_{10}$ cycloalkyl or $C_1$–$C_6$ alkyl;

$R^2$ is independently selected from:
  a) hydrogen,
  b) aryl, $C_3$–$C_{10}$ cycloalkyl, $R^{10}O$—, —$N(R^{10})_2$, F or $C_2$–$C_6$ alkenyl,
  c) $C_1$–$C_6$ alkyl unsubstituted or substituted by aryl, $C_3$–$C_{10}$ cycloalkyl, $C_2$–$C_6$ alkenyl, $R^{10}O$—, or —$N(R^{10})_2$;

$R^3$ is selected from:
  a) hydrogen,
  b) unsubstituted or substituted aryl, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

$R^4$ is selected from H, halogen, $C_1$–$C_6$ alkyl and $CF_3$;

$R^{6a}$, $R^{6b}$, $R^{6c}$, $R^{6d}$ and $R^{6e}$ are independently selected from:
  a) hydrogen,
  b) unsubstituted or substituted aryl, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—$CH_2$—, —$(CH_2)_4$— and —$(CH_2)_3$—;

$R^8$ is independently selected from:
  a) hydrogen,
  b) aryl, substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, $(R^{10})_2NC(O)$—, CN, $NO_2$, $(R^{10})_2N$—$C(NR^{10})$—, $R^{10}C(O)$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2NC(O)$—, $(R^{10})_2N$—$C(NR^{10})$—, $R^{10}C(O)$—, —$N(R^{10})_2$, or $R^{11}OC(O)NR^{10}$—;

$R^{9a}$ and $R^{9b}$ are independently hydrogen, ethyl, cyclopropyl or methyl;

$R^{10}$ is independently selected from hydrogen, $C_1$–$C_6$ alkyl, amino-$C_1$–$C_6$ alkyl, N-(unsubstituted or substituted benzolyl)-amino-$C_1$–$C_6$ alkyl, $(C_1$–$C_6$ alkyl)$_2$-amino-$C_1$–$C_6$ alkyl, acetylamino-$C_1$–$C_6$ alkyl, phenyl-$C_1$–$C_6$ alkyl, 2,2,2-trifluoroethyl, aryl and substituted aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, aryl, substituted aryl, $C_1$–$C_6$ perfluoroalkyl, 2-aminoethyl and 2,2,2-trifluoroethyl;

$A^1$ is selected from: a bond, —C(O)—, O, —N($R^{10}$)—, or S(O)$_m$;

X is a bond, —CH=CH—, —C(O)NR$^{10}$—, —NR$^{10}$C(O)—, —NR$^{10}$—, O or —C(=O)—, n is 0 or 1; provided that n is not 0 if $A^1$ is a bond, O, —N($R^{10}$)— or S(O)$_m$;

m is 0, 1 or 2;

p is 0, 1, 2, 3 or 4; and r is 0, 1 or 2;

or a pharmaceutically acceptable salt thereof.

5. The compound according to claim 3 of the formula F-1:

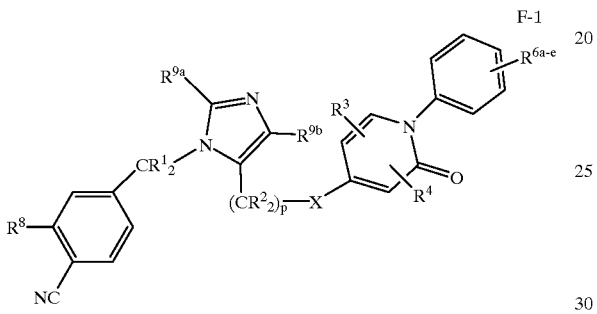

F-1 wherein:

$R^1$ is selected from: hydrogen, $C_3$–$C_{10}$ cycloalkyl or $C_1$–$C_6$ alkyl;

$R^2$ is independently selected from:
a) hydrogen,
b) aryl, $C_3$–$C_{10}$ cycloalkyl, $R^{10}$O—, —N($R^{10}$)$_2$ or F,
c) $C_1$–$C_6$ alkyl unsubstituted or substituted by aryl, $C_3$–$C_{10}$ cycloalkyl, $R^{10}$O—, or —N($R^{10}$)$_2$;

$R^3$ is selected from:
a) hydrogen,
b) unsubstituted or substituted aryl, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)NR$^{10}$—, ($R^{10}$)$_2$NC(O)—, $R^{10}{}_2$N—C(NR$^{10}$)—, CN, NO$_2$, $R^{10}$C(O)—, N$_3$, —N($R^{10}$)$_2$, or $R^{11}$OC(O)NR$^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)NR$^{10}$—, ($R^{10}$)$_2$NC(O)—, $R^{10}{}_2$N—C(NR$^{10}$)—, CN, $R^{10}$C(O)—, N$_3$, —N($R^{10}$)$_2$, and $R^{11}$OC(O)—NR$^{10}$—;

$R^4$ is selected from H, halogen, $CH_3$ and $CF_3$;

$R^{6a}$, $R_{6b}$, $R^{6c}$, $R_{6d}$ and $R^{6e}$ are independently selected from:
a) hydrogen,
b) unsubstituted or substituted aryl, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)NR$^{10}$—, ($R^{10}$)$_2$NC(O)—, $R^{10}{}_2$N—C(NR$^{10}$)—, CN, NO$_2$, $R^{10}$C(O)—, N$_3$, —N($R^{10}$)$_2$, or $R^{11}$OC(O)NR$^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)NR$^{10}$—, ($R^{10}$)$_2$NC(O)—, $R^{10}{}_2$N—C(NR$^{10}$)—, CN, $R^{10}$C(O)—, N$_3$, —N($R^{10}$)$_2$, and $R^{11}$OC(O)—NR$^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

$R^8$ is independently selected from:
a) hydrogen,
b) aryl, substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{10}$O—, $R^{10}$C(O)NR$^{10}$—, ($R^{10}$)$_2$NC(O)—, CN, NO$_2$, ($R^{10}$)$_2$N—C(NR$^{10}$)—, $R^{10}$C(O)—, —N($R^{10}$)$_2$, or $R^{11}$OC(O)N$^{10}$—, and
c) $C_1$–$C_6$ alkyl substituted by $C_1$–$C_6$ perfluoroalkyl, $R^{10}$O—, $R^{10}$C(O)NR$^{10}$—, ($R^{10}$)$_2$NC(O)—, ($R^{10}$)$_2$N—C(NR$^{10}$)—, $R^{10}$C(O)—, —N($R^{10}$)$_2$, or $R^{11}$OC(O)NR$^{10}$—;

$R^{9a}$ and $R^{9b}$ are independently hydrogen, ethyl, cyclopropyl or methyl;

$R^{10}$ is independently selected from hydrogen, $C_1$–$C_6$ alkyl, amino-$C_1$–$C_6$ alkyl, N-(unsubstituted or substituted benzolyl)-amino-$C_1$–$C_6$ alkyl, ($C_1$–$C_6$ alkyl)$_2$-amino-$C_1$–$C_6$ alkyl, acetylamino-$C_1$–$C_6$ alkyl, phenyl-$C_1$–$C_6$ alkyl, 2,2,2-trifluoroethyl, aryl and substitute aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, aryl, substituted aryl, $C_1$–$C_6$ perfluoroalkyl, 2-aminoethyl and 2,2,2-trifluoroethyl;

X is a bond, —CH=CH—, —C(O)NR$^{10}$—, —NR$^{10}$C(O)—, —NR$^{10}$—, O or —C(=O)—;

m is 0, 1 or 2; and p is 0, 1, 2, 3 or 4;

or a pharmaceutically acceptable salt thereof.

6. The compound according to claim 4 of the formula G-1:

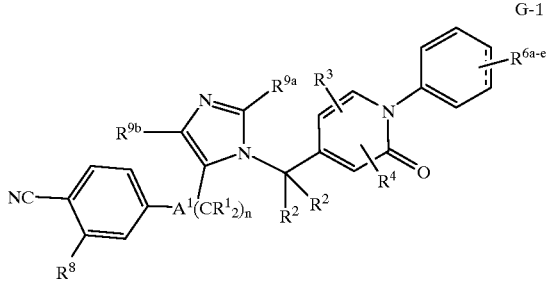

G-1 wherein:

$R^1$ is selected from: hydrogen, $C_3$–$C_{10}$ cycloalkyl, $R^{10}$O—, —N($R^{10}$)$_2$, F or $C_1$–$C_6$ alkyl;

$R^2$ is independently selected from:
a) hydrogen,
b) aryl or $C_3$–$C_{10}$ cycloalkyl,
c) $C_1$–$C_6$ alkyl unsubstituted or substituted by aryl, $C_3$–$C_{10}$ cycloalkyl, $C_2$–$C_6$ alkenyl, $R^{10}$O—, or —N($R^{10}$)$_2$;

$R^3$ is selected from:

a) hydrogen,
b) unsubstituted or substituted aryl, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

$R^4$ is selected from H, halogen, $CH_3$ and $CF_3$;

$R^{6a}$, $R^{6b}$, $R^{6c}$, $R^{6d}$ and $R^{6e}$ are independently selected from:
a) hydrogen,
b) unsubstituted or substituted aryl, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

$R^8$ is independently selected from:
a) hydrogen,
b) aryl, substituted aryl, $C_1$–$C_6$ alkyl, $C_2$–$C_6$ alkenyl, $C_2$–$C_6$ allkynyl, $C_1$–$C_6$ perfluoroalkyl, F, Cl, $R^{10}O$—, $R^{10}C(O)NR^{10}$—, $(R^{10})_2NC(O)$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2NC(O)$—, $(R^{10})_2N$—$C(NR^{10})$—, $R^{10}C(O)$—, —$N(R^{10})_2$, or $R^{11}OC(O)NR^{10}$—;

$R^{9a}$ and $R^{9b}$ are independently hydrogen, ethyl, cyclopropyl or methyl;

$R^{10}$ is independently selected from hydrogen, $C_1$–$C_6$ alkyl, amino-$C_1$–$C_6$ alkyl, N-(unsubstituted or substituted benzolyl)-amino-$C_1$–$C_6$ alkyl, ($C_1$–$C_6$ alkyl)$_2$-amino-$C_1$–$C_6$ alkyl, acetylamino-$C_1$–$C_6$ alkyl, phenyl-$C_1$–$C_6$ alkyl, 2,2,2-trifluoroethyl, aryl and substituted aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, aryl, substituted aryl, $C_1$–$C_6$ perfluoroalkyl, 2-aminoethyl and 2,2,2-trifluoroethyl;

$A^1$ is selected from: a bond, —C(O)—, O, —N($R^{10}$)—, or S(O)$_m$;

m is 0, 1 or 2; and n is 0 or 1;

or a pharmaceutically acceptable salt thereof.

7. A compound which is selected from:

4-[3-(2-Oxo-1-phenyl-1,2-dihydropyridin-4-ylmethyl)-3H-imidazol-4-ylmethyl]benzonitrile (L-799,266)

4-{3-[1-(3-Chloro-phenyl)-2-oxo-1,2-dihydropyridin-4-ylmethyl]-3H-imidazol-4-ylmethyl}benzonitrile (L-799,521)

4-{3-[1-(3-Chloro-phenyl)-2-oxo-1,2-dihydro-pyridin-4-ylmethyl]-3H-imidazol-4-ylmethyl}-2-methoxy-benzonitrile 4-{5-[1-(3-Chloro-phenyl)-2-oxo-1,2-dihydro-pyridin-4-ylmethyl]-imidazol-1-ylmethyl}-2-methoxy-benzonitrile or a pharmaceutically acceptable salt thereof.

8. The compound according to claim 7 which is:

4-[3-(2-Oxo-1-phenyl-1,2-dihydropyridin-4-ylmethyl)-3H-imidazol-4-ylmethyl]benzonitrile

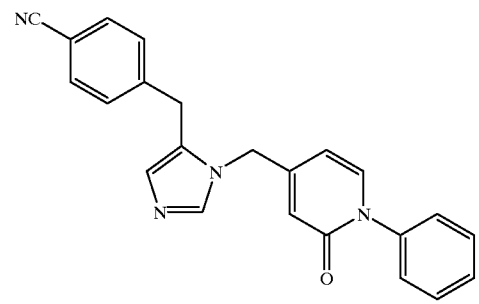

or a pharmaceutically acceptable salt thereof.

9. The compound according to claim 7 which is:

4-{3-[1-(3-Chloro-phenyl)-2-oxo-1,2-dihydropyridin-4-ylmethyl]-3H-imidazol-4-ylmethyl}benzonitrile

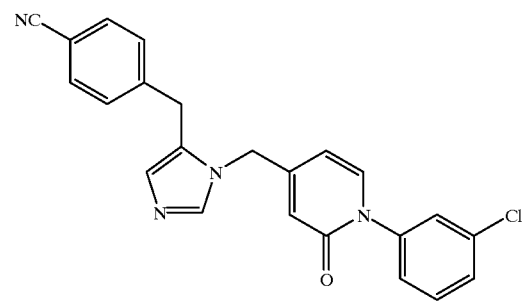

or a pharmaceutically acceptable salt thereof.

10. The compound according to claim 7 which is:

4-{5-[1-(3-Chloro-phenyl)-2-oxo-1,2-dihydro-pyridin-4-ylmethyl]-imidazol-1-ylmethyl}-2-methoxy-benzonitrile

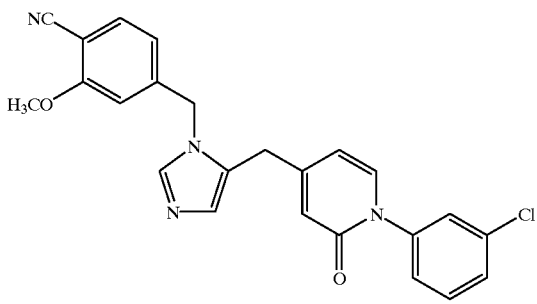

or a pharmaceutically acceptable salt thereof.

11. A pharmaceutical composition comprising a pharmaceutical carrier, and dispersed therein, a therapeutically effective amount of a compound of claim 1.

12. A pharmaceutical composition comprising a pharmaceutical carrier, and dispersed therein, a therapeutically effective amount of a compound of claim 1.

13. A pharmaceutical composition comprising a pharmaceutical carrier, and dispersed therein, a therapeutically effective amount of a compound of claim 7.

14. A pharmaceutical composition made by combining the compound of claim 1 and a pharmaceutically acceptable carrier.

15. A process for making a pharmaceutical composition comprising combining a compound of claim 1 and a pharmaceutically acceptable carrier.

16. A pharmaceutical composition made by combining the compound of claim 2 and a pharmaceutically acceptable carrier.

17. A process for making a pharmaceutical composition comprising combining a compound of claim 2 and a pharmaceutically acceptable carrier.

18. A method for inhibiting farnesyl-protein transferase in treating cancer which comprises administering to a mammal in need thereof a therapeutically effective amount of a composition of claim 11.

19. A method for inhibiting farnesyl-protein transferase in treating cancer which comprises administering to a mammal in need thereof a therapeutically effective amount of a composition of claim 12.

20. A method for inhibiting farnesyl-protein transferase in treating cancer which comprises administering to a mammal in need thereof a therapeutically effective amount of a composition of claim 13.

* * * * *